US012788886B2

(12) United States Patent
Dasbach et al.

(10) Patent No.: US 12,788,886 B2
(45) Date of Patent: Nov. 10, 2026

(54) DRUG DELIVERY DEVICE

(71) Applicant: SANOFI, Paris (FR)

(72) Inventors: Uwe Dasbach, Frankfurt am Main (DE); Katrin Rapp, Frankfurt am Main (DE); Hugo Revellat, Niort (FR); Thomas Mark Kemp, Cambridgeshire (GB); Robbie Wilson, Cambridgeshire (GB)

(73) Assignee: Sanofi, Paris (FR)

( * ) Notice: Subject to any disclaimer, the term of this patent is extended or adjusted under 35 U.S.C. 154(b) by 428 days.

(21) Appl. No.: 17/046,150

(22) PCT Filed: Apr. 9, 2019

(86) PCT No.: PCT/EP2019/058866
§ 371 (c)(1),
(2) Date: Oct. 8, 2020

(87) PCT Pub. No.: WO2019/197360
PCT Pub. Date: Oct. 17, 2019

(65) Prior Publication Data

US 2021/0030963 A1 Feb. 4, 2021

(30) Foreign Application Priority Data

Apr. 11, 2018 (EP) .................................... 18305432

(51) Int. Cl.
*A61M 5/20* (2006.01)
*A61M 5/28* (2006.01)
(Continued)

(52) U.S. Cl.
CPC .......... *A61M 5/2033* (2013.01); *A61M 5/286* (2013.01); *A61M 5/3158* (2013.01);
(Continued)

(58) Field of Classification Search
CPC .. A61M 5/2033; A61M 5/50; A61M 5/14248; A61M 5/286; A61M 5/3158;
(Continued)

(56) References Cited

U.S. PATENT DOCUMENTS

2009/0088689 A1* 4/2009 Carter ............... A61M 5/14248 604/151
2012/0123387 A1* 5/2012 Gonzalez .......... A61M 37/0015 604/506
(Continued)

FOREIGN PATENT DOCUMENTS

CN 102497909 6/2012
CN 102686255 A 9/2012
(Continued)

OTHER PUBLICATIONS

International Preliminary Report on Patentability in International Appln. No. PCT/EP2019/058866, dated Oct. 13, 2020, 10 pages.
(Continued)

*Primary Examiner* — Bhisma Mehta
*Assistant Examiner* — Fatimata Sahra Diop
(74) *Attorney, Agent, or Firm* — Fish & Richardson P.C.

(57) ABSTRACT

A drug delivery device comprises a housing adapted to receive a primary package, the housing comprising a distal surface adapted to be placed against an injection site and a proximal surface opposite the distal surface, the proximal surface adapted to be held in the palm of a user's hand during drug delivery, the housing having a flat form-factor in such a manner that a first extension of the housing between the distal surface and the proximal surface is less than at least one extension at right angles to the first extension.

16 Claims, 21 Drawing Sheets

(51) Int. Cl.
*A61M 5/315* (2006.01)
*A61M 5/32* (2006.01)

(52) U.S. Cl.
CPC ... *A61M 5/3202* (2013.01); *A61M 2005/2013* (2013.01); *A61M 2205/13* (2013.01); *A61M 2205/581* (2013.01)

(58) Field of Classification Search
CPC ........ A61M 5/3202; A61M 2005/2013; A61M 2005/14252; A61M 2005/14256; A61M 2005/1426; A61M 2005/2073; A61M 2005/208; A61M 2005/24; A61M 2005/31518; A61M 2005/3267; A61M 2005/3268; A61M 2205/13; A61M 2205/581; A61M 2005/13
See application file for complete search history.

(56) References Cited

U.S. PATENT DOCUMENTS

| | | | | |
|---|---|---|---|---|
| 2014/0148784 | A1* | 5/2014 | Anderson | A61M 5/14248 604/150 |
| 2015/0320939 | A1* | 11/2015 | Beek | A61M 5/326 604/193 |
| 2015/0335829 | A1* | 11/2015 | Giambattista | A61M 5/2033 |
| 2016/0082242 | A1* | 3/2016 | Burton | A61M 5/14248 604/173 |
| 2016/0228644 | A1 | 8/2016 | Cabiri | |
| 2017/0182243 | A1* | 6/2017 | Cole | A61M 5/14248 |
| 2017/0348488 | A1 | 12/2017 | Bechmann et al. | |
| 2017/0368260 | A1* | 12/2017 | McCullough | A61M 5/20 |
| 2019/0366000 | A1* | 12/2019 | Cowe | A61M 5/2422 |

FOREIGN PATENT DOCUMENTS

| | | | | |
|---|---|---|---|---|
| CN | 102883759 | | 1/2013 | |
| CN | 104428020 | A | 3/2015 | |
| CN | 104884104 | A | 9/2015 | |
| CN | 105828854 | A | 8/2016 | |
| JP | 2013-500773 | | 1/2013 | |
| JP | 2014-502884 | A | 2/2014 | |
| JP | 2014-502886 | | 2/2014 | |
| JP | 2014-503300 | A | 2/2014 | |
| JP | 2014-503303 | A | 2/2014 | |
| JP | 2014-515669 | | 7/2014 | |
| JP | 2021-520890 | | 8/2021 | |
| WO | WO 2006/111859 | | 10/2006 | |
| WO | WO-2006111859 | A1 * | 10/2006 | A61M 5/2033 |
| WO | WO 2011/014514 | | 2/2011 | |
| WO | WO 2011/048223 | A1 | 4/2011 | |
| WO | WO 2011/090955 | | 7/2011 | |
| WO | WO 2012/085027 | A1 | 6/2012 | |
| WO | WO 2012/085030 | | 6/2012 | |
| WO | WO 2012/093070 | A1 | 7/2012 | |
| WO | WO 2012/093073 | A1 | 7/2012 | |
| WO | WO 2012/145752 | | 10/2012 | |
| WO | WO 2014/001318 | A2 | 1/2014 | |
| WO | WO 2014/082959 | A1 | 6/2014 | |
| WO | WO 2015/087090 | A2 | 6/2015 | |
| WO | WO 2017/062938 | A1 | 4/2017 | |
| WO | WO 2018/028915 | A1 | 2/2018 | |
| WO | WO 2019/197361 | | 10/2019 | |

OTHER PUBLICATIONS

PCT International Search Report and Written Opinion in International Appln. No. PCT/EP2019/058866, dated Jun. 13, 2019, 14 pages.

* cited by examiner

DRUG DELIVERY DEVICE

CROSS REFERENCE TO RELATED APPLICATIONS

The present application is the national stage entry of International Patent Application No. PCT/EP2019/058866, filed on Apr. 9, 2019, and claims priority to Application No. EP 18305432.9, filed on Apr. 11, 2018, the disclosures of which are incorporated herein by reference.

TECHNICAL FIELD

The disclosure generally relates to a drug delivery device.

BACKGROUND

Drug delivery devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

SUMMARY

An object of the present disclosure is to provide an improved drug delivery device.

The object is achieved by a drug delivery device according to claim 1.

Exemplary embodiments are provided in the dependent claims.

According to the present disclosure a drug delivery device comprises a housing adapted to receive a primary package, the housing comprising a distal surface adapted to be placed against an injection site and a proximal surface opposite the distal surface, the proximal surface adapted to be held in the palm of a user's hand during drug delivery, the housing having a flat form-factor in such a manner that a first extension of the housing between the distal surface and the proximal surface is less than at least one extension at right angles to the first extension.

In an exemplary embodiment, the drug delivery device comprises an injection needle configured to be connected or connectable to a primary package received within the housing. In particular, the needle comprises a first tip which is automatically movable relative with respect to the housing between a retracted position hidden within the housing and an extended position extending through the distal surface of the housing.

According to the present disclosure, the needle comprises a first tip which is either configured:

- to be extended beyond the distal surface by a manual operation, or
- to extend beyond the distal surface and to be covered by a shroud configured to be retracted to expose the first tip by a manual operation.

In an exemplary embodiment, a mounting axis of the primary package is essentially at right angles with respect to the first extension.

In an exemplary embodiment, the distal surface is non-adhesive.

In an exemplary embodiment, the distal surface is rigid.

In an exemplary embodiment, the needle is part of a needle module and comprises a second tip adapted to pierce a septum on a primary package received within the housing.

In an exemplary embodiment, the needle is a single needle bent at approximately 90 degrees. In further exemplary embodiments, or the first tip and the second tip of the needle are separate from each other and arranged at approximately 90 degrees to each other and for example connected within a solid block or via a flexible tube.

In an exemplary embodiment, the drug delivery device comprises a trigger adapted to move the needle relatively with respect to the housing from the retracted position to the extended position upon manual operation of the trigger. In an exemplary embodiment, the trigger may comprise at least one of a shroud, at least one button and a body contact sensor. The shroud is for example configured as a needle shroud which is for example movable between an extended position covering the needle, in particular its first tip and a retracted position uncovering the needle, in particular its first tip. In a further embodiment, the body contact sensor and the needle shroud form a single trigger assembly.

In an exemplary embodiment, the at least one button is disposed at the proximal surface or at at least one lateral surface or at a rear surface of the housing.

In an exemplary embodiment, the drug delivery device comprises a carrier adapted to mount a primary package. Furthermore, the primary package may be movable substantially in parallel with the distal surface of the housing between a rearward position, in which the second tip is spaced from the septum and a forward position, in which the second tip pierces the septum. For example, the primary package is relatively movable with respect to at least one of the carrier, the trigger and the housing to pierce the septum by the needle. Alternatively, the carrier with the mounted primary package may be relatively movable with respect to at least one of the trigger and the housing to pierce the septum by the needle.

In an exemplary embodiment, the button is adapted to be locked prior to operation of the shroud or body contact sensor preventing operation of the button. Furthermore, the button is adapted to be unlocked for example upon operation of the shroud or body contact sensor allowing operation of the button.

In an exemplary embodiment, the drug delivery device comprises a drive spring adapted to apply a force in a forward direction to a piston of the primary package. In particular, the drug delivery device may further comprise a plunger adapted to propagate the force from the drive spring to the piston.

In an exemplary embodiment, the drug delivery device comprises a primary package containing a medicament. For example, the primary package is formed as a cartridge or a container containing a medicament.

In an exemplary embodiment, the needle module is coupled with or integrated in a button such that depression of the button in the distal direction moves the needle module in the distal direction.

In an exemplary embodiment, a shroud spring is arranged to bias the shroud in the distal direction against the housing or against the needle module or against the button.

According to an aspect of the present disclosure, a method of using the drug delivery device described above comprises taking the housing with a hand such that the proximal surface is located within a palm of the hand, placing the distal surface on an injection site. A first tip of the needle is either extended beyond the distal surface by a manual operation, e.g. depression of a trigger, or extends beyond the distal surface and is covered by a shroud and this shroud is retracted to expose the first tip by a manual operation. The drug delivery device is then held on the injection site during an injection time.

According to the present disclosure, a drug delivery device, in particular an auto-injector with a flat form-factor or low profile is provided, in particular adapted to facilitate an injection essentially perpendicular to a mounting axis of a primary pack, e.g. a drug cartridge. Flat form-factor or low profile means that a height of the drug delivery device is substantially less than its width. The flat form-factor of the device provides superior handling and usability as opposed to a conventional pen-shaped auto-injector.

The drug delivery device may be used as a single-use disposable, shroud activated auto-injector, operated by patients for self-administration or by health care professionals to others. The flat-format facilitates optimised ergonomics for longer duration of injections, reduced effort and pain for those with impairments, and reduced susceptibility to unintentional movements during an injection.

The drug delivery device may be adapted to retain the primary pack sealed until pierced at the moment of injection or immediately prior to this.

As opposed to a conventional pen injector, the presently described flat form-factor drug delivery device helps prevent leaking of the medicament, yields a higher stability during longer injection times (e.g. more than 15 s) because it is easier for the user to hold a flat form-factor drug delivery device against the injection site without flinching or altering the orientation than with a conventional pen injector. Long injection times allow for using the drug delivery device with high viscosity drugs.

Moreover, the flat format allows for improved discretion during injection allowing users to inject themselves in public. Furthermore, the flat-format has a considerably increased skin contact surface as opposed to conventional pen injectors which results in a reduced contact pressure.

In an exemplary embodiment, the distal surface may be rigid so as to maintain its shape when placed against an injection site. In another an exemplary embodiment, the distal surface may be flexible.

In an exemplary embodiment, the distal surface is not adhesive, i.e. it does not have an adhesive applied to it. The presently claimed drug delivery device is thus a handheld device whereas conventional patch devices are intended to be adhesively connected to the injection site and not handheld during injection.

In an exemplary embodiment, the distal surface may have anti-skid properties, e.g. due to a surface structure or a coating.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge. The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
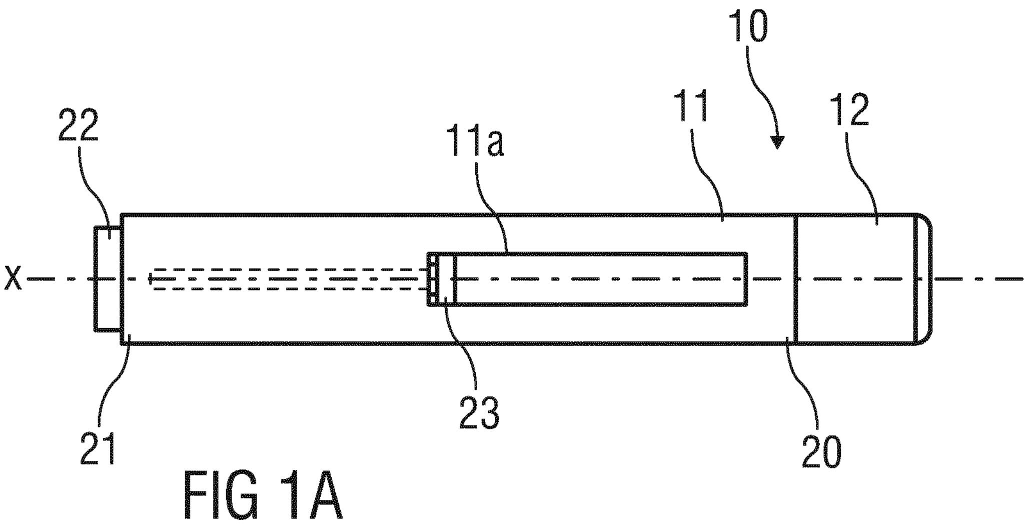
FIGS. 1A and 1B are schematic views of an exemplary embodiment of a drug delivery device.
Figure 1B:
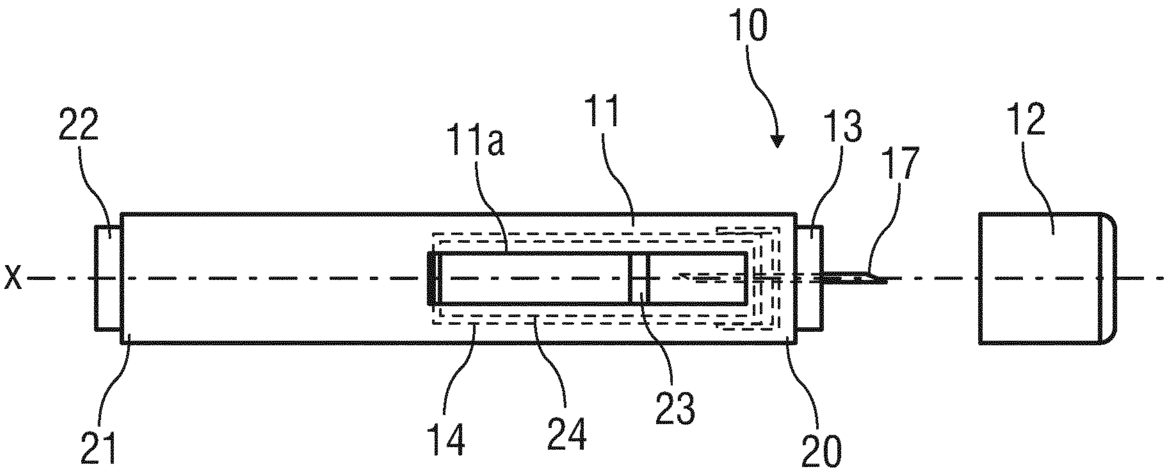

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a primary package 24 or a container or syringe) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11. Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11*a* through which the syringe 24 can be monitored.

Figure 2A:
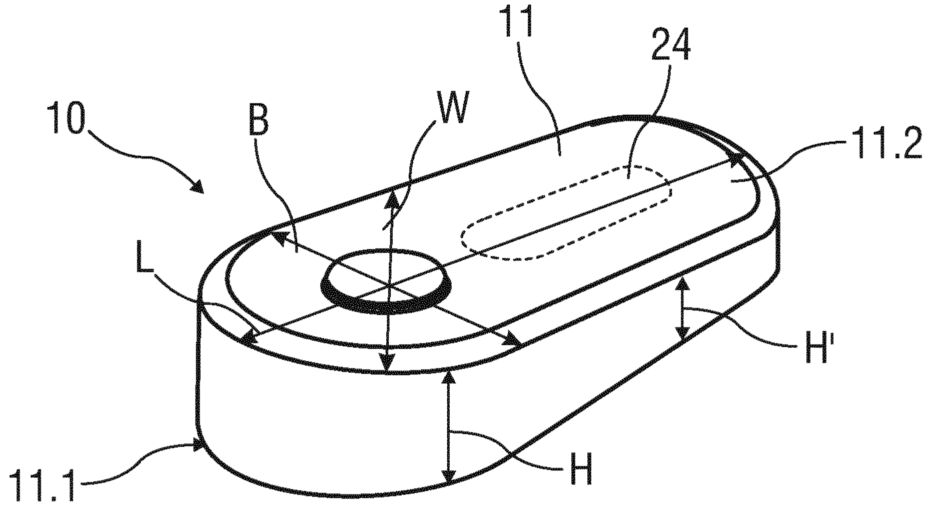
FIG. 2A is a schematic view of an exemplary embodiment of a housing of a drug delivery device.

FIG. 2A is a schematic perspective view of an exemplary embodiment of a drug delivery device 10 comprising a housing 11 adapted to contain a primary package 24, e.g. a cartridge or a container containing a medicament. As shown, housing 11 is substantially flat, i.e. it has a distal surface 11.1.

The distal surface 11.1 is adapted to be placed against an injection site. The housing 11 further comprises a proximal surface 11.2 opposite the distal surface 11.1. The proximal surface 11.2 is configured as a gripping surface, e.g. to be held in the palm of a user's hand during drug delivery.

In an exemplary embodiment, the distal surface 11.1 has a flat outer surface. Alternatively, the distal surface 11.1 may be bent in an inward direction of the housing 11 or has a concave shape.

In an exemplary embodiment, the proximal surface 11.2 is bent in an outward direction of the housing 11 or has a convex shape.

The housing 11 has a flat form-factor in such a manner that at least a first extension H of the housing 11 between the distal surface 11.1 and the proximal surface 11.2 is less than at least one extension L at right angles to the first extension H.

In an exemplary embodiment, the first extension H or any other varied first extensions H' of the housing 11 between the distal surface 11.1 and the proximal surface 11.2 is less than any other extension L, B, W at right angles to the first extensions H, H'. In other words: The first extension H represents the height of the device 10. The height of the device 10, in particular the height of the housing 11, may vary. The at least one first extension H and/or H' is or are less than each of the other extensions L, B, W of the device 10, wherein the other extensions L, B, W for instance represent the length, the width and/or a diagonal of the device 10.

In an exemplary embodiment, a mounting axis of the primary package 24 is essentially at right angles with respect to the first extension H or H'.

The distal surface 11.1 may be configured non-adhesive. It allows better user comfort. Furthermore, the distal surface 11.1 is rigid.

Figure 2B:
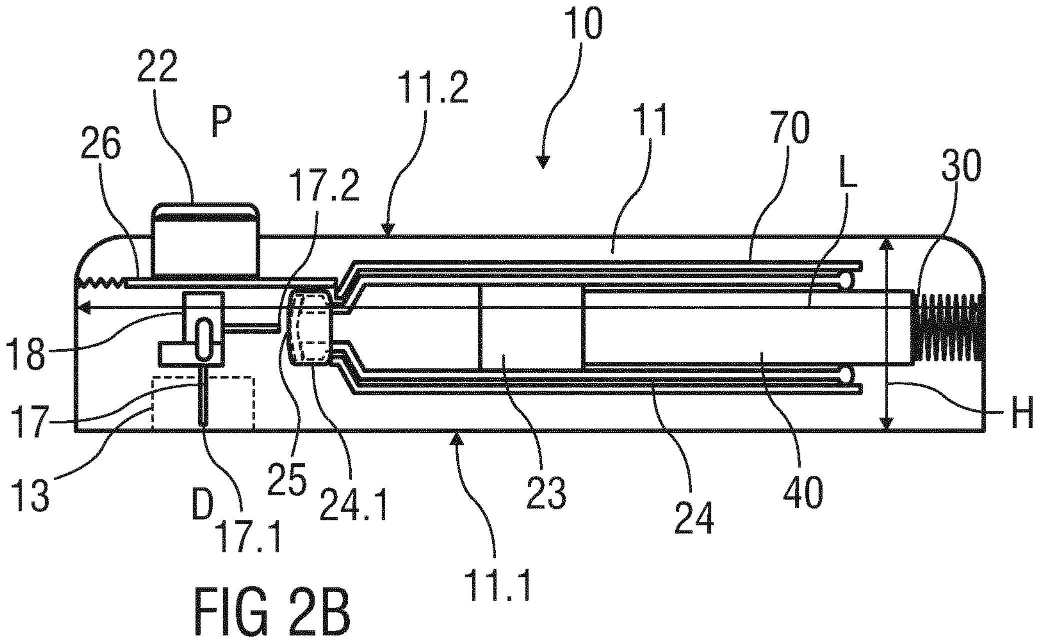
FIG. 2B is a schematic view of an exemplary embodiment of a drug delivery device.

FIG. 2B is a schematic perspective view of an exemplary embodiment of a drug delivery device 10. A housing 11 of the drug delivery device 10 has a similar flat-form-factor as of the housing 11 in FIG. 2A.

The housing 11 is adapted to contain a primary package 24. As shown, housing 11 is substantially flat, i.e. it has a distal surface 11.1 in parallel with a longest axis of the drug delivery device 10 and substantially in parallel with a longitudinal axis of the primary package 24. The distal surface 11.1 is intended to be directed towards an injection site during injection and adapted to rest on the injection site. The housing 11 may be configured to resemble a computer mouse.

The term "distal" refers to a location that is relatively closer to a site of injection, and the term "proximal" refers to a location that is relatively further away from the injection site.

Device 10 can also include a needle shroud 13 coupled to the housing 11 to permit movement of the shroud 13 relative to the housing 11. For example, the shroud 13 can move in a proximal direction P or in a distal direction D. Specifically, movement of the shroud 13 in a proximal direction can permit a needle 17 to extend from the distal surface 11.1 of housing 11.

The term "forward" refers to a location that is relatively close to the needle 17 along the longest axis of the drug delivery device 10, and the terms "rear" or "rearward" refer to a location that is relatively further away from the needle 17 along the longest axis of the drug delivery device 10.

Insertion of the needle 17 can occur via several mechanisms. For example, the needle 17 may be fixedly located relative to housing 11 and initially be located within an extended needle shroud 13. Proximal movement of the shroud 13 by placing a distal end of shroud 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the shroud 13.

In another form of "manual" insertion the needle 17 is coupled to a button 22 and moves relative to housing 11 as the button 22 is moved. As shown in FIG. 2, button 22 is located at a proximal surface 11.2 of the housing 11. However, in other embodiments, button 22 could be located on a side of housing 11.

Another form of insertion is "automated," whereby the needle 17 moves relative to housing 11. Such insertion can be triggered by movement of shroud 13 or by another form of activation, such as, for example, a button 22. As shown in FIG. 2, button 22 is located at a proximal surface 11.2 of the housing 11. However, in other embodiments, button 22 could be located on a side of housing 11. In further embodiments, the button 22 has been deleted and is replaced for instance by a shroud trigger mechanism, e.g. provided by pushing the needle shroud 13 inside the housing when the drug delivery device is put onto an injection side.

Other manual or automated features can include drug injection or needle retraction, or both. Injection is the process by which a bung or piston 23 is moved from a rearward location within a primary package 24, container or syringe to a more forward location within the primary package 24 in order to force a medicament from the primary package 24 through needle 17.

In some embodiments, an energy source, e.g. a drive spring may be arranged and under compression before device 10 is activated. One end of the drive spring can be fixed within the housing 11, and another end of the drive spring can be configured to apply a compressive force to a surface of piston 23. Following activation, at least part of the energy stored in the drive spring can be applied to the piston 23. This compressive force can act on piston 23 to move it to displace the liquid medicament from the primary package 24.

Following injection, the needle 17 can be retracted within shroud 13 or housing 11. Retraction can occur when shroud 13 moves distally as a user removes device 10 from a patient's body. This can occur as needle 17 remains fixedly located relative to housing 11. Once a distal end of the shroud 13 has moved past a distal end of the needle 17, and the needle 17 is covered, the shroud 13 can be locked. Such locking can include locking any proximal movement of the shroud 13 relative to the housing 11.

Another form of needle retraction can occur if the needle 17 is moved relative to the housing 11. Following sufficient retraction, any relative movement between the needle 17 and the housing 11 can be locked with a locking mechanism. In addition, button 22 or other components of device 10 can be locked as required.

The needle 17 is part of a needle module 18 and has a first tip 17.1 adapted to extend from the distal surface 11.1 and a second tip 17.2 extending essentially in parallel with the distal surface 11.1 within the housing 11 towards the primary package 24 and adapted to pierce a septum 25 arranged on a forward end 24.1 of the primary package 24 to establish a fluid communication between the needle 17 and a cavity within the primary package 24 filled with the medicament. The primary package 24 may be adapted to be moved substantially in parallel with the distal surface 11.1 towards the needle module 18 to allow the second tip 17.2 to pierce the septum 25.

In an exemplary embodiment, the needle 17 may comprise a single needle 17 bent at approximately 90 degrees. In another exemplary embodiment, the needle module 18 may comprise a solid block 19 and the needle 17 may comprise two separate needle tips 17.1, 17.2 arranged at 90 degrees to each other and connected within the solid block. In yet another exemplary embodiment, the two separate needle tips 17.1, 17.2 are arranged at 90 degrees to each other and connected via a flexible connector, e.g. a tubing.

The shroud 13 may be configured as a trigger to initiate movement of the primary package 24 towards the needle module 18 and movement of the needle 17 in the distal direction D to extend from the distal surface 11.1.

In an exemplary embodiment, a button 22 is provided, e.g. on the proximal surface 11.2 to initiate movement of the primary package 24 towards the needle module 18 and movement of the needle 17 in the distal direction D to extend from the distal surface 11.1. In this case, the shroud 13 may be used as a safety interlock, allowing operation of the button 22 only when the shroud 13 is depressed into the housing 11 in the proximal direction P. In another embodiment, operation of the trigger button 22 may be possible regardless of the position of the shroud 13 but the drug delivery device 10 may be configured to ignore operation of the trigger button 22 unless the shroud 13 is depressed into the housing first. In yet another embodiment, initiation of movement of the primary package 24 towards the needle module 18 and movement of the needle 17 in the distal direction D to extend from the distal surface 11.1 may require depression of the shroud 13 and operation of the button 22 regardless of the order of these actions.

In yet another embodiment, a button 22 may not be provided and movement of the primary package 24 towards the needle module 18 and movement of the needle 17 in the distal direction D to extend from the distal surface 11.1 may be initiated only be depression of the shroud 13.

A plunger 40 is arranged to apply a force on the piston 23, e.g. driven by a drive spring.

Figure 3:
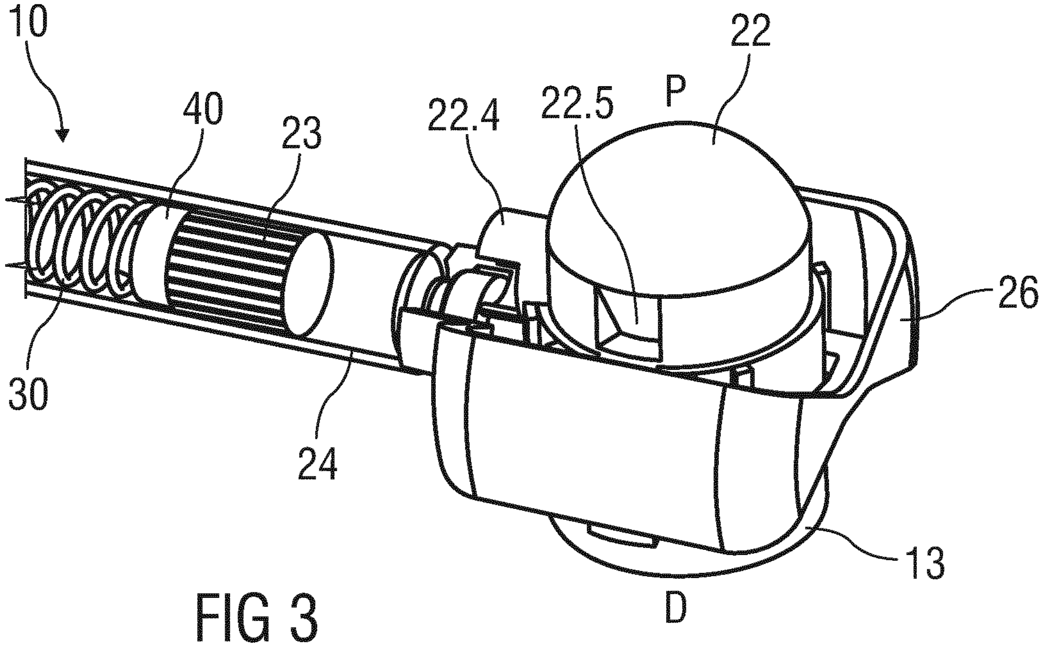
FIG. 3 is a schematic view of an exemplary embodiment of a drug delivery device.
Figure 4:
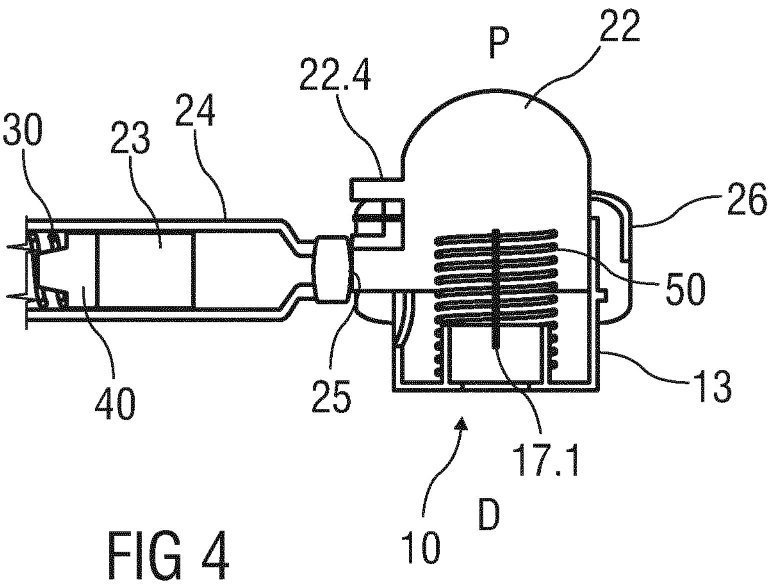
FIG. 4 is a schematic view of the drug delivery device.
Figure 5:
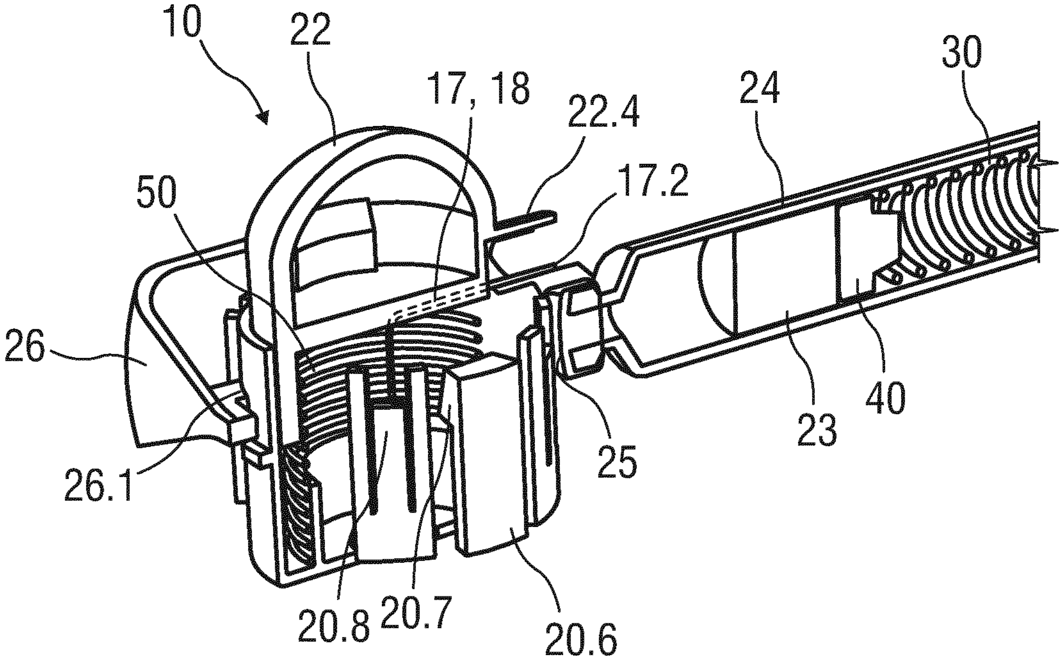
FIG. 5 is a schematic view of the drug delivery device.

FIGS. 3, 4 and 5 are different views of an exemplary embodiment of a drug delivery device 10 configured essentially like the one shown in FIG. 2.

The primary package 24 is slidable in the forward direction between a locking position and a release position. A shroud 13 is slidable in the distal direction D and in the proximal direction P such that the shroud 13 may extend from the distal surface 11.1 and be depressed towards the housing 11 into a retracted position. A needle module 18 having a needle 17 with a first tip 17.1 and a second tip 17.2 is provided, the first tip 17.1 adapted to be extended from the distal surface 11.1 and the second tip adapted to point towards the primary package 24 to pierce a septum 25 thereof.

A drive spring 30 is arranged to bias the plunger 40 to displace the piston 23 within the primary package 24 to deliver a dose and to bias the primary package 24 in the forward direction.

Figure 9:
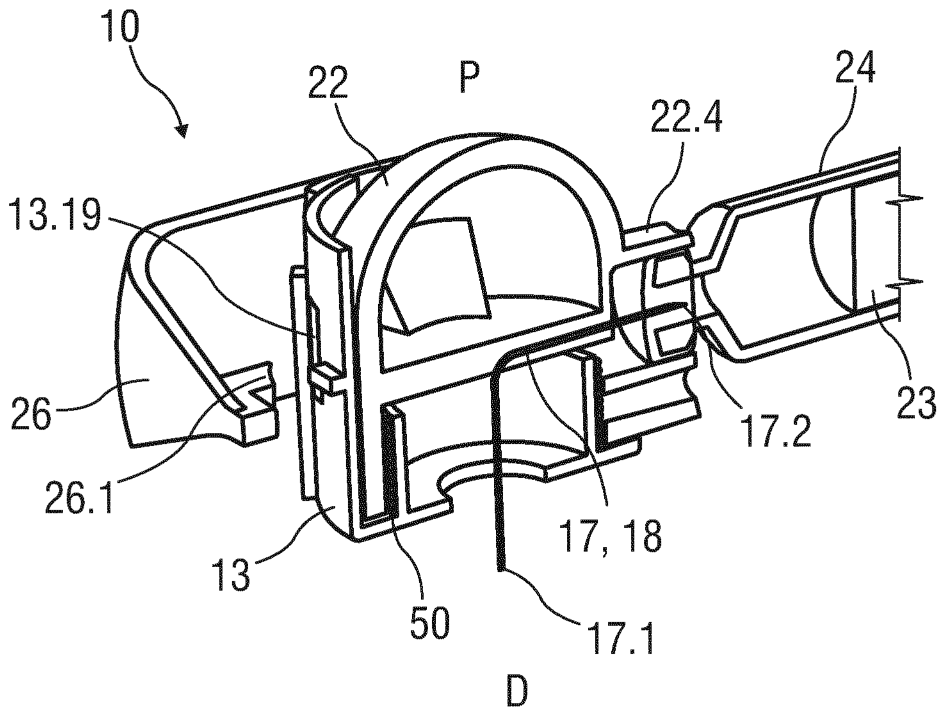
FIG. 9 is a schematic view of the drug delivery device after depression of the button.

A latch chassis 26 is arranged to receive a forward end of the primary package 24. As best seen in FIG. 9, the latch chassis 26 comprises at least one latch boss 26.1 adapted to engage in a latch window 13.19 in the shroud 13 so as to limit movement of the shroud 13 in the distal direction D.

The needle module 18 is coupled with or integrated in a button 22 such that depression of the button 22 in the distal direction D moves the needle module 18 in the distal direction D. The button 22 comprises a rearwardly directed sleeve 22.4 and the second tip 17.2 is essentially centered within this sleeve 22.4. The button 22 has a proximal position when not being depressed in which the sleeve 22.4 is not coaxial with the primary package 24 such that the primary package 24 abuts an edge of the sleeve 22.4 and cannot advance forward. The button 22 has a distal position when being depressed in which the sleeve 22.4 is coaxial with the primary package 24 such that the primary package 24 can advance forward into the sleeve 22.4 and the second tip 17.2 pierces the septum 25. A shroud spring 50 is arranged to bias the button 22 against the shroud 13.

A carrier 70 may be arranged within the housing 11 to contain the primary package 24 and to allow movement thereof essentially in parallel with the distal surface 11.1 towards the needle module 18.

At least one resilient button locking beam 20.6 is arranged on the housing 11, in particular on the distal region 20 thereof, the button locking beam 20.6 having a ramped inward protrusion 20.7 adapted to engage in a respective recess 22.5 within the button 22 through a slot 13.1 in the shroud 13. The shroud 13 comprises a support section 13.14 outwardly from the button locking beam 20.6 which, when the shroud 13 is in a first extended position protruding the distal surface 11.1 and/or in a second extended position protruding the distal surface 11.1 further than in the first extended position, outwardly supports the button locking beam 20.6 preventing it from deflecting outwards. At least one shroud locking beam 20.8 is arranged on the housing 11, in particular on the distal region 20 thereof, the shroud locking beam 20.8 having a ramped inward protrusion 20.9 (shown in FIG. 12) adapted to engage a surface on the shroud 13 and a surface on the button 22 through a window 13.15 in the shroud 13.

At least one shroud rib 13.16 is arranged on the shroud 13 and configured to abut the housing 11, in particular the distal region 20 thereof to prevent the shroud 13 from moving distally beyond the second extended position.

Figure 6:
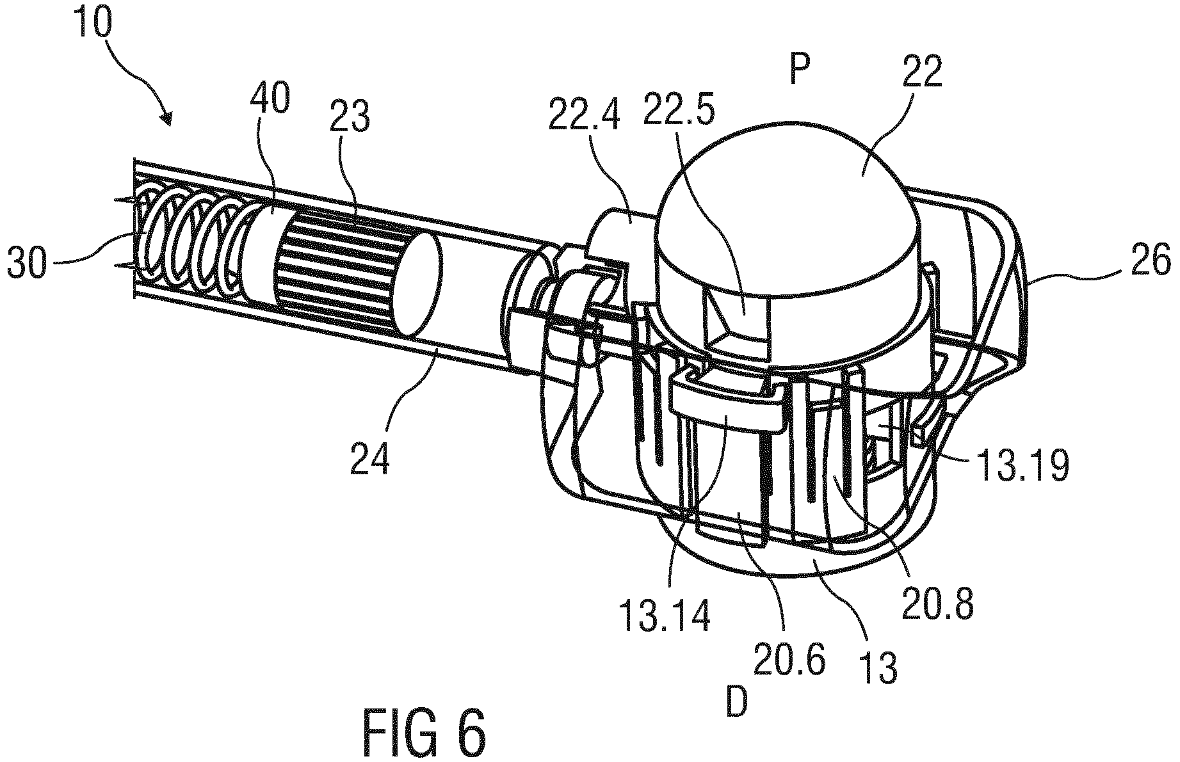
FIG. 6 is a schematic view of the drug delivery device prior to use.

FIG. 6 is a schematic view of the drug delivery device 10 prior to use. The primary package 24 is in a rearward position. The button 22 is in the proximal position such that the primary package 24 abuts an edge of the sleeve 22.4 and cannot advance forward. The shroud 13 is in the first extended position such that the support section 13.14 prevents outward deflection of the button locking beam 20.6. The ramped inward protrusion of the shroud locking beam 20.8 extends inwards through the window 13.15 preventing the shroud 13 from advancing further towards the second extended position. The button 22 distally abuts the button locking beam 20.6 and cannot be depressed as the button locking beam 20.6 cannot deflect. The needle module 18 is in the retracted position so the first tip 17.1 is hidden behind the distal surface 11.1.

Figure 7:
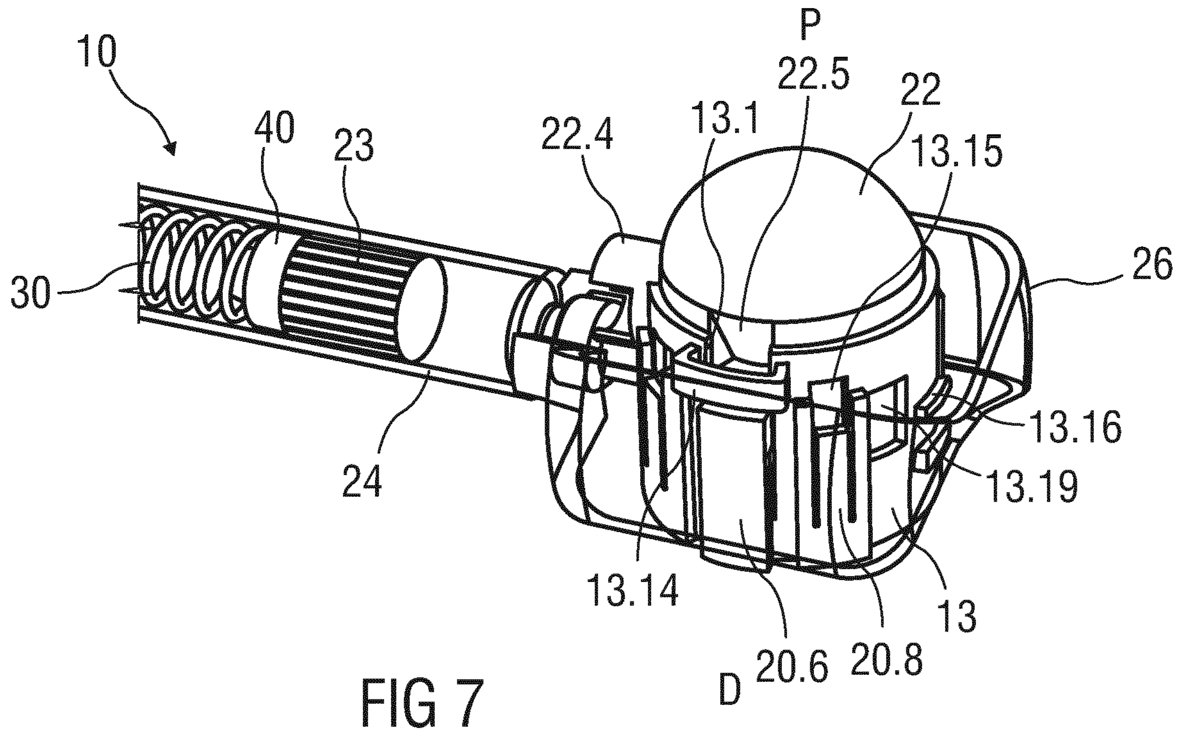
FIG. 7 is a schematic view of the drug delivery device with a shroud depressed towards a housing.

FIG. 7 is a schematic view of the drug delivery device 10 placed with the distal surface 11.1 on an injection site. The shroud 13 is depressed towards the housing 11 in the proximal direction P thereby also moving the support section 13.14 in the proximal direction such that the support section 13.14 does no longer outwardly support the button locking beam 20.6, allowing depression of the button 22.

Figure 8:
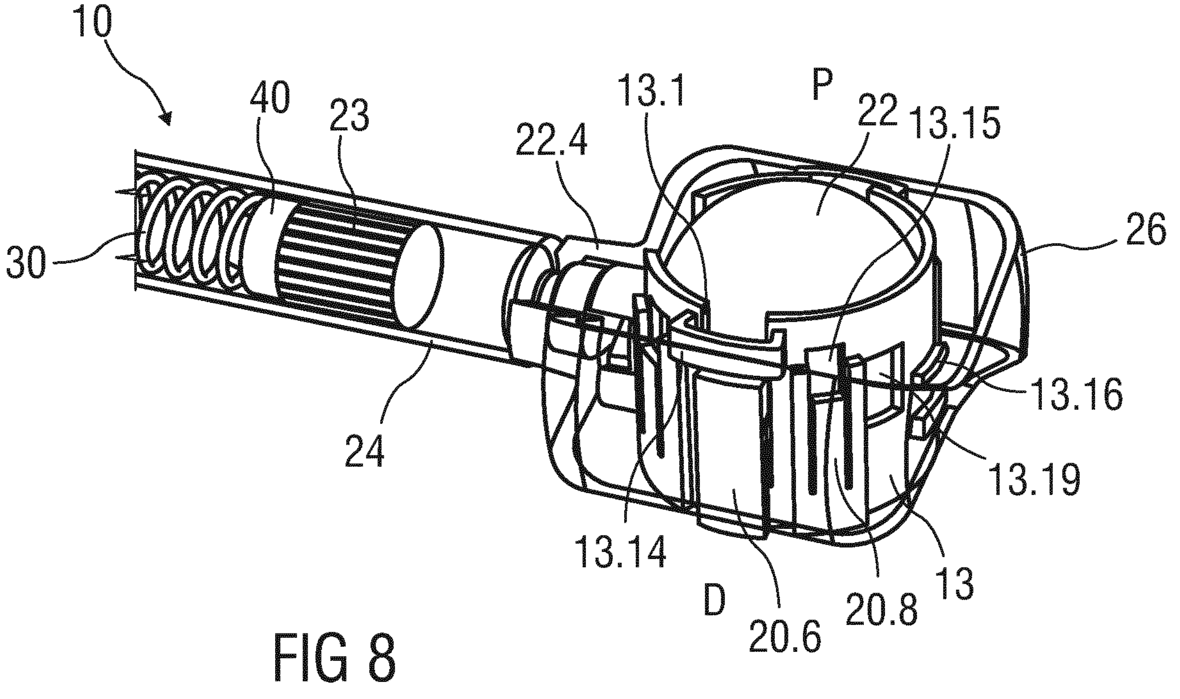
FIG. 8 is a schematic view of the drug delivery device during depression of a button.

FIG. 8 is a schematic view of the drug delivery device 10 upon depression of the button 22 in the distal direction D into the distal position. As the button 22 is moved it deflects the button locking beam 20.6 outwards and, upon further depression of the button 22, allows it to relax into the recess 22.5 thus locking the button 22 in the distal position. The movement of the button 22 also moves the needle module 18 in the distal direction D such that the first tip 17.1 of the needle extends from the distal surface 11.1 into the injection site. Moreover, during the movement, the button 22 engages the ramp inward protrusion 20.9 of the shroud locking beam 20.8 and deflects the shroud locking beam 20.8 sufficiently outward to prevent the shroud locking beam 20.8 from abutting a proximal end of the window 13.15 so the shroud 13 can advance beyond the first extended position when being re-advanced later.

FIG. 9 is a schematic view of the drug delivery device 10 after depression of the button 22. Towards the end of the movement of the button 22, the sleeve 22.4 becomes coaxial with the primary package 24 such that the primary package 24 can advance forward into the sleeve 22.4, driven by the drive spring 30, and the second tip 17.2 pierces the septum 25 allowing the drive spring 30 to dispense the dose by displacing the piston 23. As the primary package 24 advances, the latch chassis 26 also advances disengaging the latch boss 26.1 from the latch window 13.19.

Figure 10:
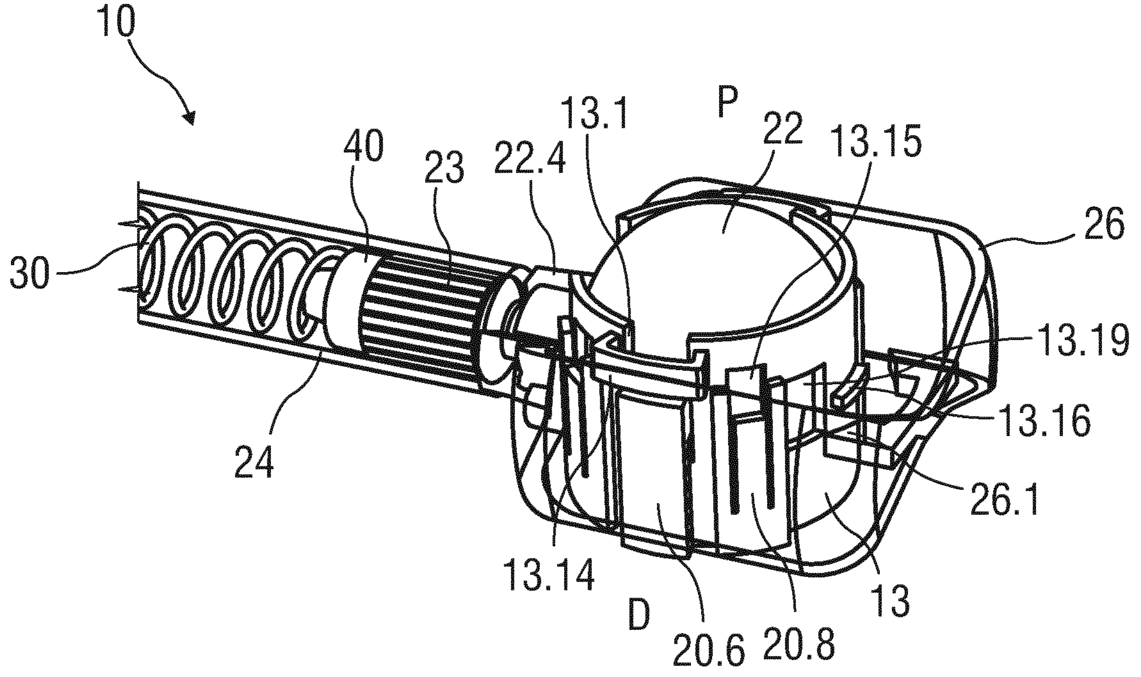
FIG. 10 is a schematic view of the drug delivery device at an end of dose.

FIG. 10 is a schematic view of the drug delivery device 10 at the end of dose with the piston 23 having bottomed out in the primary package 24.

Figure 11:
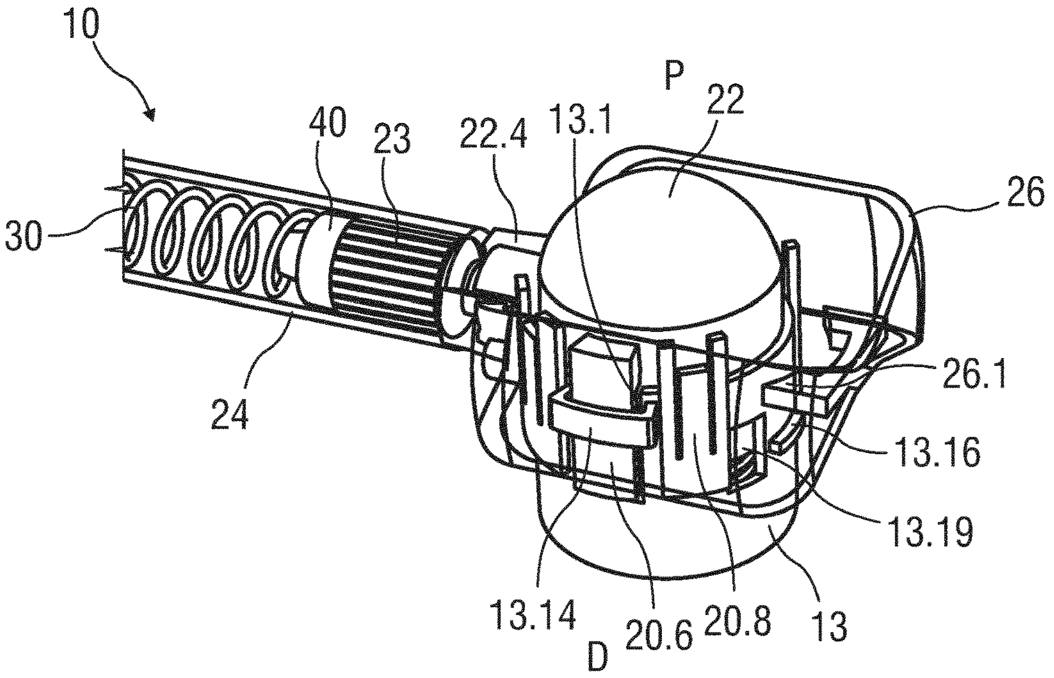
FIG. 11 is a schematic view of the drug delivery device after removal from an injection site.
Figure 12:
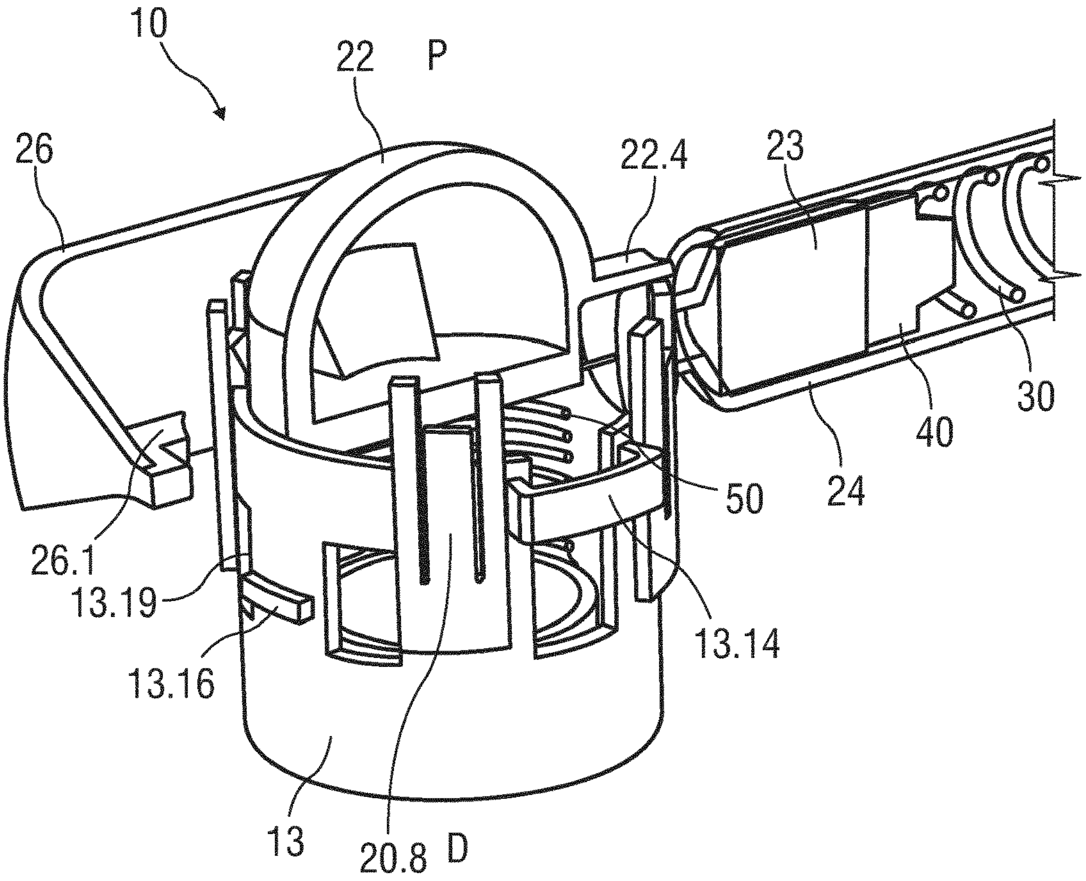
FIG. 12 is a schematic view of the drug delivery device after removal from the injection site.

FIGS. 11 and 12 are schematic views of the drug delivery device 10 after removal from the injection site. The shroud 13 is no longer depressed so the shroud spring 50 moves the shroud 13 in the distal direction D into the second extended position so as to cover the distal tip 17.1. As the latch boss 26.1 has disengaged from the latch window 13.19 the shroud 13 can travel further in the distal direction D than initially. As the button 22 has outwardly deflected the shroud locking beam 20.8, the shroud locking beam 20.8 does not abut the proximal end of the window 13.15 when the shroud 13 is being advanced. Instead, the proximal end of the window 13.15 engages the ramp on the inward protrusion 20.9 of the shroud locking beam 20.8, deflecting the shroud locking beam 20.8 further outwards during continued movement of the shroud 13. Once the shroud 13 arrives in the second extended position, the shroud rib 13.16 abuts the housing 11 stopping further movement of the shroud 13 in the distal direction D, the proximal end of the shroud 13 passes the inward protrusion 20.9, the shroud locking beam 20.8 relaxes inwards and the shroud 13 is locked in the second extended position by the inward protrusion 20.9.

Figure 13:
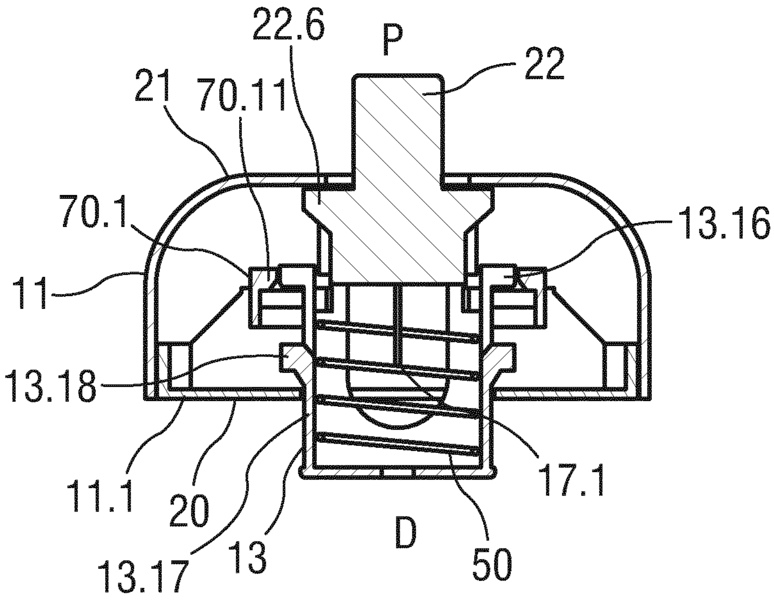
FIG. 13 is a schematic view of another exemplary embodiment of a drug delivery device prior to use.
Figure 14:
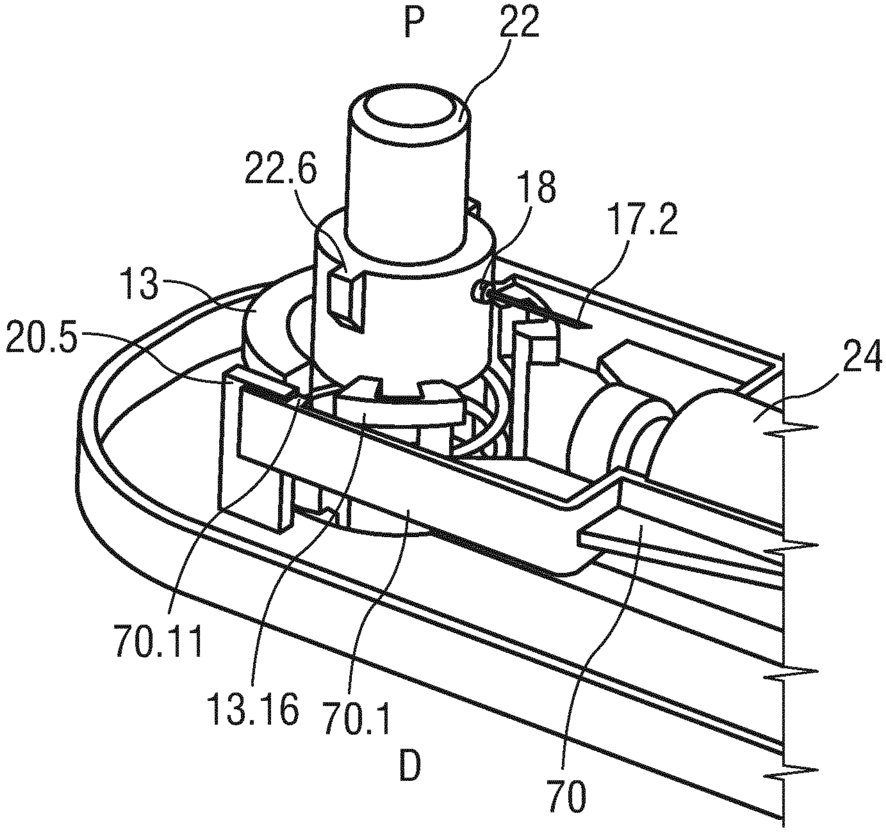
FIG. 14 is a schematic view of the drug delivery device.

FIGS. 13 and 14 are schematic views of an exemplary embodiment of a drug delivery device 10 configured essentially like the one shown in FIG. 2.

The primary package 24 is slidable in the forward direction from a locking position to a release position. A shroud 13 is slidable in the distal direction D and in the proximal direction P such that the shroud 13 may extend from the distal surface 11.1 and be depressed towards the housing 11 from an extended position into a retracted position. A needle module 18 having a needle 17 with a first tip 17.1 and a second tip 17.2 is provided, the first tip 17.1 adapted to be extended from the distal surface 11.1 and the second tip adapted to point towards the primary package 24 to pierce a septum (not shown) thereof.

A drive spring (not shown) is arranged to bias the plunger (not shown) to displace the piston (not shown) within the primary package 24 to deliver a dose and to bias the primary package 24 in the forward direction.

The needle module 18 is coupled with or integrated in a button 22 such that depression of the button 22 in the distal direction D moves the needle module 18 in the distal direction D. The button 22 has a proximal position when not being depressed in which second tip 17.2 is not coaxial with the primary package 24. The button 22 has a distal position when being depressed in which the second tip 17.2 is coaxial with the primary package 24 such that the second tip 17.2 can pierce the septum 25. A shroud spring 50 is arranged to bias the button 22 against the shroud 13.

A carrier 70 may be arranged within the housing 11 to contain the primary package 24 and to allow movement thereof essentially in parallel with the distal surface 11.1 towards the needle module 18. The carrier 70 comprises at least one resilient forward arm 70.1 having a front surface 70.11 configured to abut on a stop 20.5 on the housing 11, in particular on the distal region 20 thereof thus maintaining the carrier 70 and the primary package 24 in a rearward position.

The shroud 13 comprises at least one resilient arm 13.17 having an outward protrusion 13.18 configured to be in the vicinity of one respective forward arm 70.1 when the shroud 13 is in the retracted position such that outward deflection of the resilient arm 13.17 causes outward deflection of the forward arm 70.1 so that the front surface 70.11 disengages the stop 20.5 allowing the carrier 70 to move forward. The button 22 comprises at least one ramped protrusion 22.6 configured to engage the resilient arm 13.17 upon depression of the button 22 into the distal position when the shroud 13 is in the retracted position such that the resilient arm 13.17 is outwardly deflected and disengages the forward arm 70.1 from the stop 20.5. The skilled person understands that either the protrusion 22.6 or the resilient arm 13.17 or both can be ramped to achieve this deflection.

The forward arms 70.1 may comprise snap features adapted to engage corresponding features on the shroud 13 when the carrier 70 is in the forward position and when the shroud 13 is advanced into the extended position.

At least one shroud rib 13.16 may be arranged on the shroud 13 and configured to abut the forward arm 70.1 of the carrier to prevent the shroud 13 from moving distally beyond the extended position. In an alternative embodiment, the shroud rib 13.16 may abut the housing 11, in particular the distal region 20 thereof to prevent the shroud 13 from moving distally beyond the extended position.

FIGS. 13 and 14 show the drug delivery device 10 prior to use. The primary package 24 is in a rearward position. The button 22 is in the proximal position. The needle module 18 is in the retracted position so the first tip 17.1 is hidden behind the distal surface 11.1. The forward arms 70.1 of the carrier abut the stop 20.5 such that the primary package 24 cannot advance forward. The shroud 13 is in the extended position such that the outward protrusion 13.18 is located distally from the forward arm 70.1 or at least from a protrusion thereon having the front surface 70.11. Depression of the button 22 in this state would thus not cause release of the forward arms 70.1 from the stop 20.5.

Figure 15:
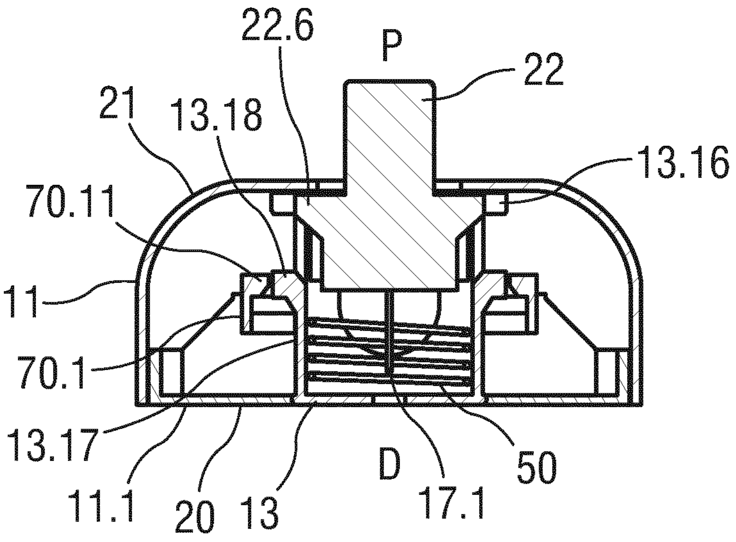
FIG. 15 is a schematic view of the drug delivery device with a shroud depressed towards a housing.
Figure 16:
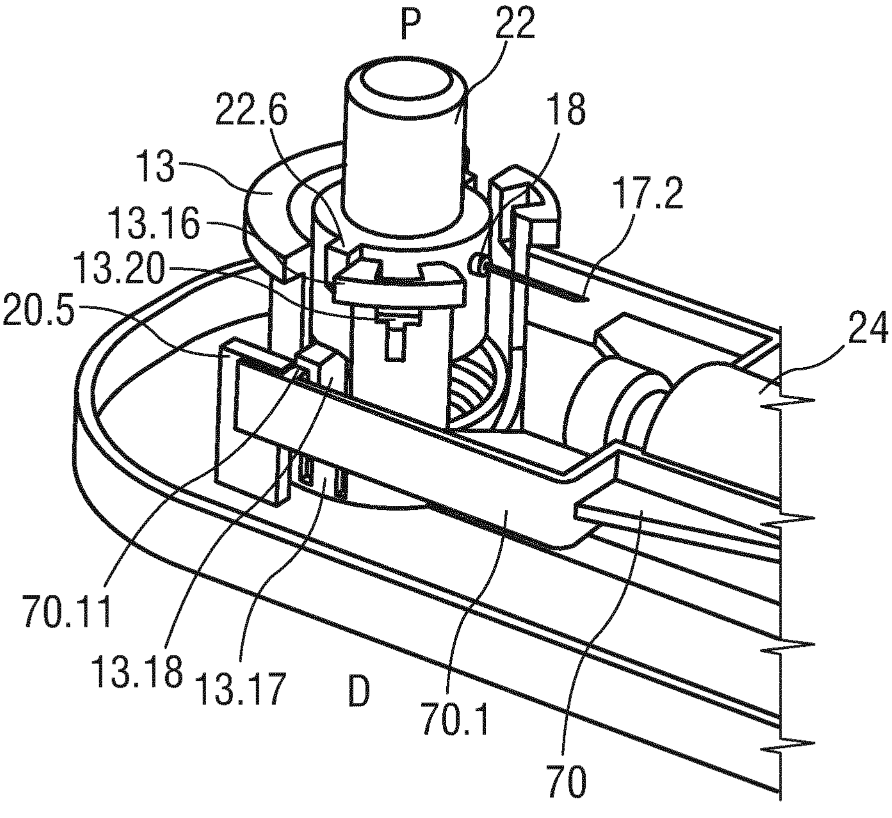
FIG. 16 is a schematic view of the drug delivery device with the shroud depressed towards the housing.

FIGS. 15 and 16 are schematic views of the drug delivery device 10 placed with the distal surface 11.1 on an injection site. The shroud 13 is depressed towards the housing 11 in the proximal direction P thus aligning the outward protrusion 13.18 with the forward arm 70.1, i.e. bringing the outward protrusion 13.18 into the vicinity of the forward arm 70.1.

Figure 17:
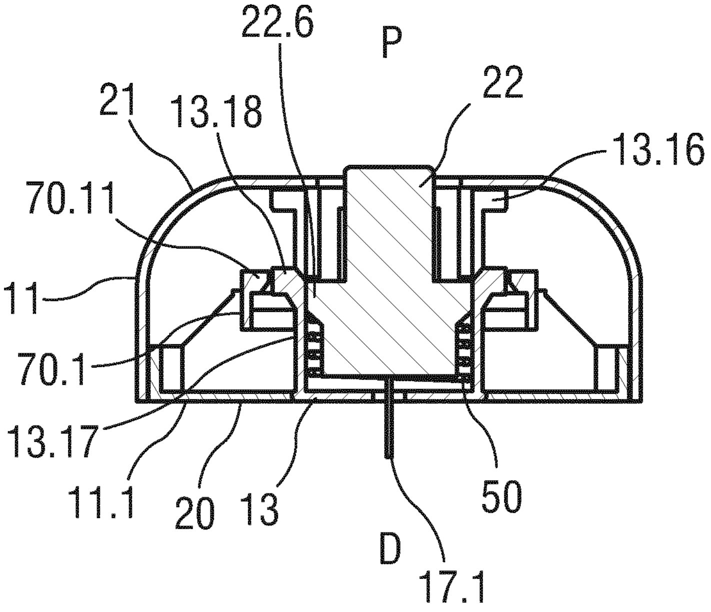
FIG. 17 is a schematic view of the drug delivery device during depression of a button.
Figure 18:
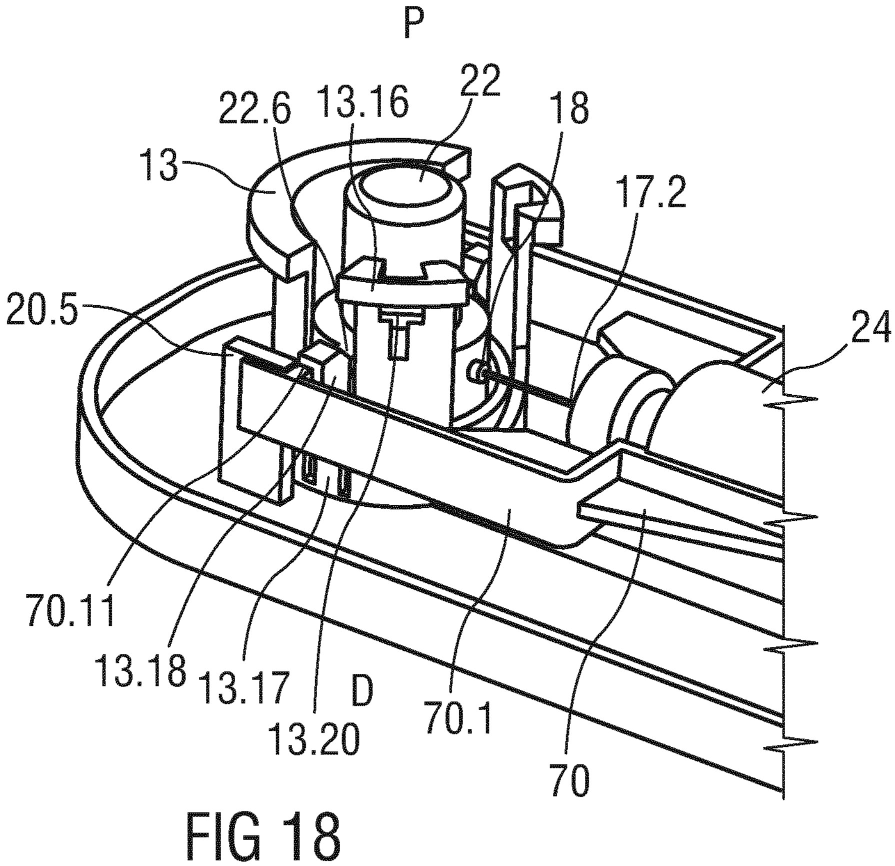
FIG. 18 is a schematic view of the drug delivery device during depression of the button.

FIGS. 17 and 18 are schematic views of the drug delivery device 10 upon depression of the button 22 in the distal direction D into the distal position. As the button 22 is moved the protrusion 22.6 on the button 22 engages the resilient arm 13.17 and deflects it outwards thus disengaging the forward arm 70.1 from the housing 11.

The movement of the button 22 also moves the needle module 18 in the distal direction D such that the first tip 17.1 of the needle extends from the distal surface 11.1 into the injection site.

Figure 19:
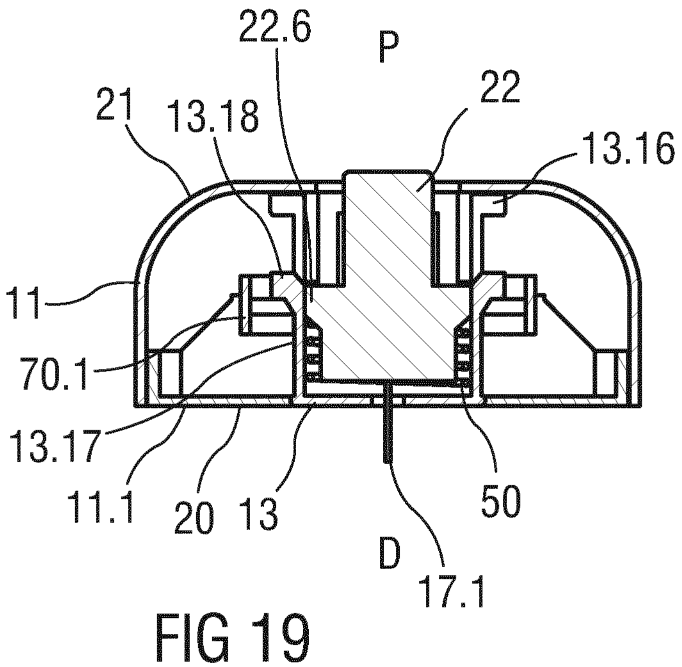
FIG. 19 is a schematic view of the drug delivery device after depression of the button.
Figure 20:
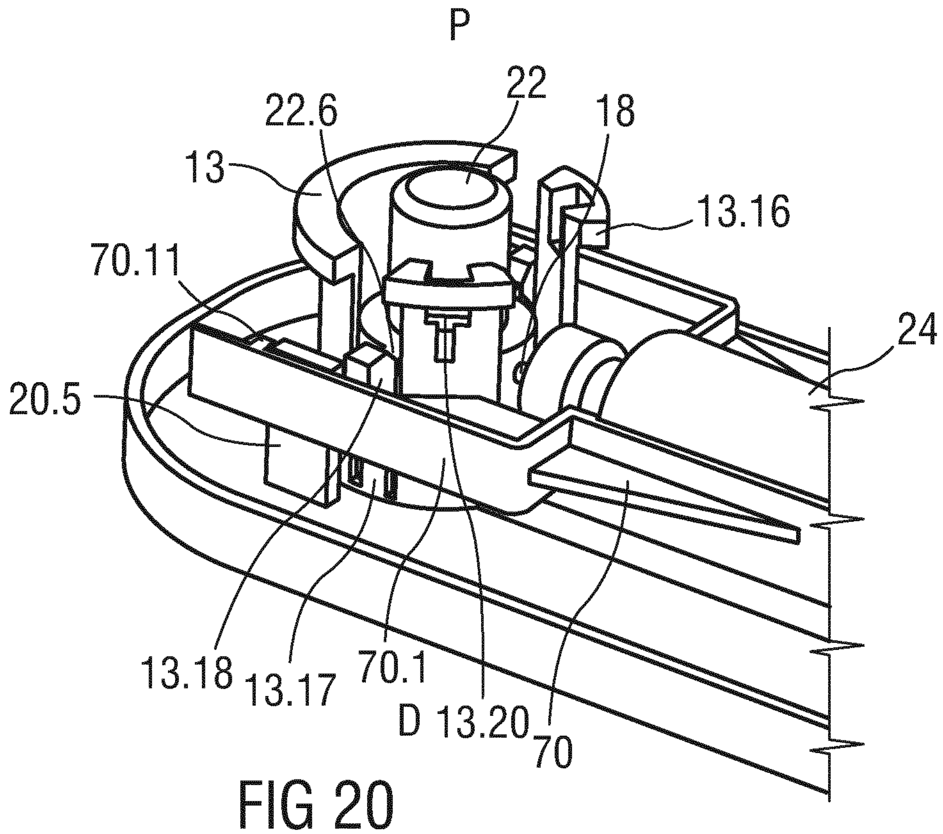
FIG. 20 is a schematic view of the drug delivery device after depression of the button.

FIGS. 19 and 20 are schematic views of the drug delivery device 10 after depression of the button 22. Due to the release of the forward arm 70.1, the carrier 70 and the primary package 24 can advance forward, driven by the drive spring, and the second tip 17.2 pierces the septum allowing the drive spring to dispense the dose by displacing the piston. In an alternative embodiment, a carrier spring may be arranged to advance the carrier 70 and primary package 24 and a drive spring may be arranged to advance the piston within the primary package 24. In this case the drive spring may act between the piston and the carrier 70 only being prevented from advancing the piston due to the medicament being unable to escape from the primary package 24 as long as the septum is not pierced. In another exemplary embodiment, a drive spring release mechanism may be arranged to lock the drive spring and release it once the carrier arrives in the forward position.

Figure 21:
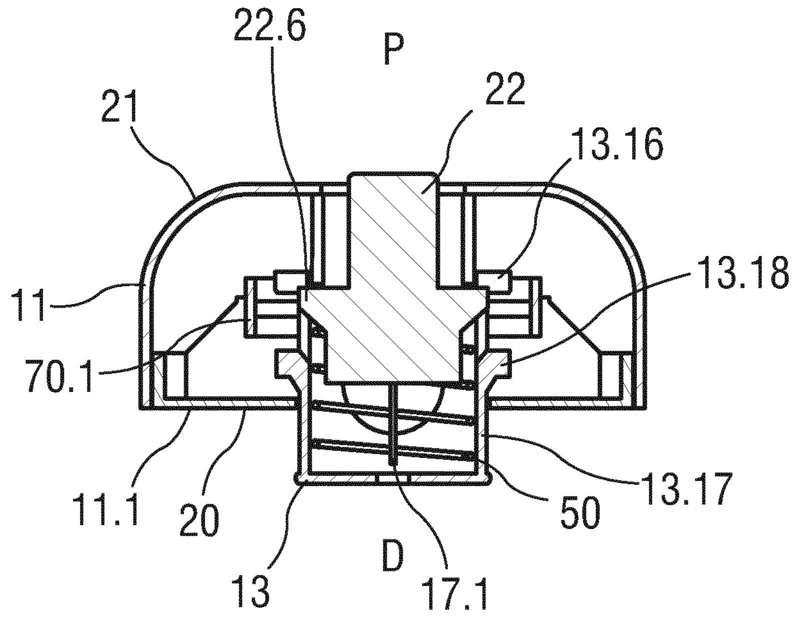
FIG. 21 is a schematic view of the drug delivery device after removal from an injection site.
Figure 22:
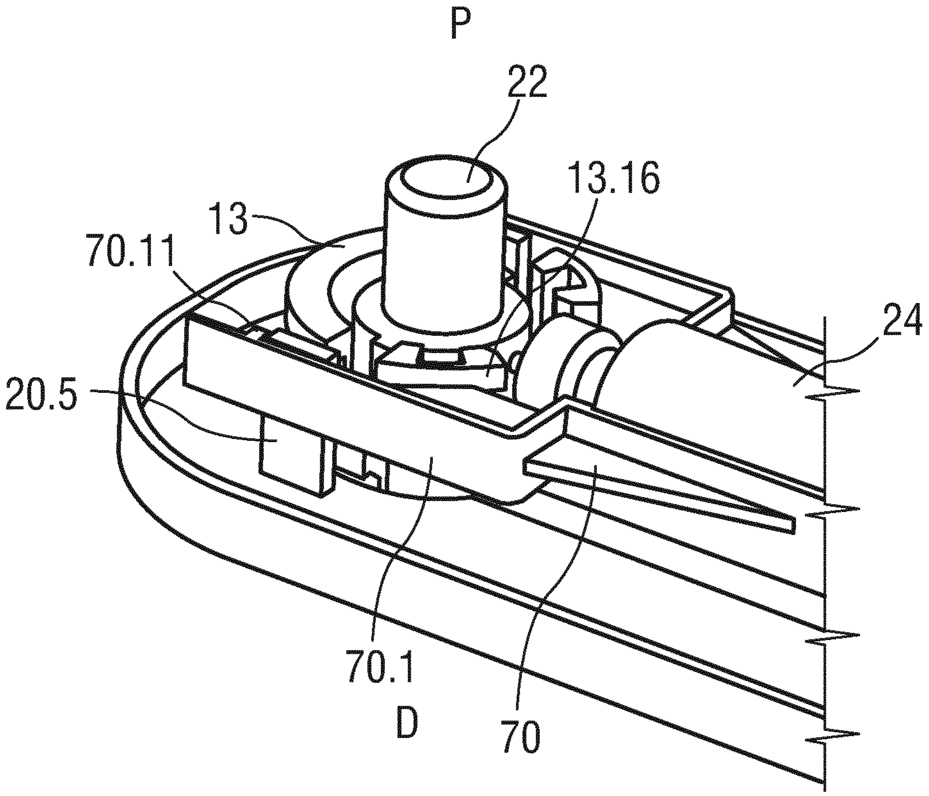
FIG. 22 is a schematic view of the drug delivery device after removal from the injection site.

FIGS. 21 and 22 are schematic views of the drug delivery device 10 after removal from the injection site. The shroud 13 is no longer depressed so the shroud spring 50 moves the shroud 13 in the distal direction D back into the extended position so as to cover the distal tip 17.1. Once the shroud 13 arrives in the extended position it may lock in place due to the above mentioned snap features on the forward arms 70.1 engaging the corresponding features on the shroud 13.

Figure 23:
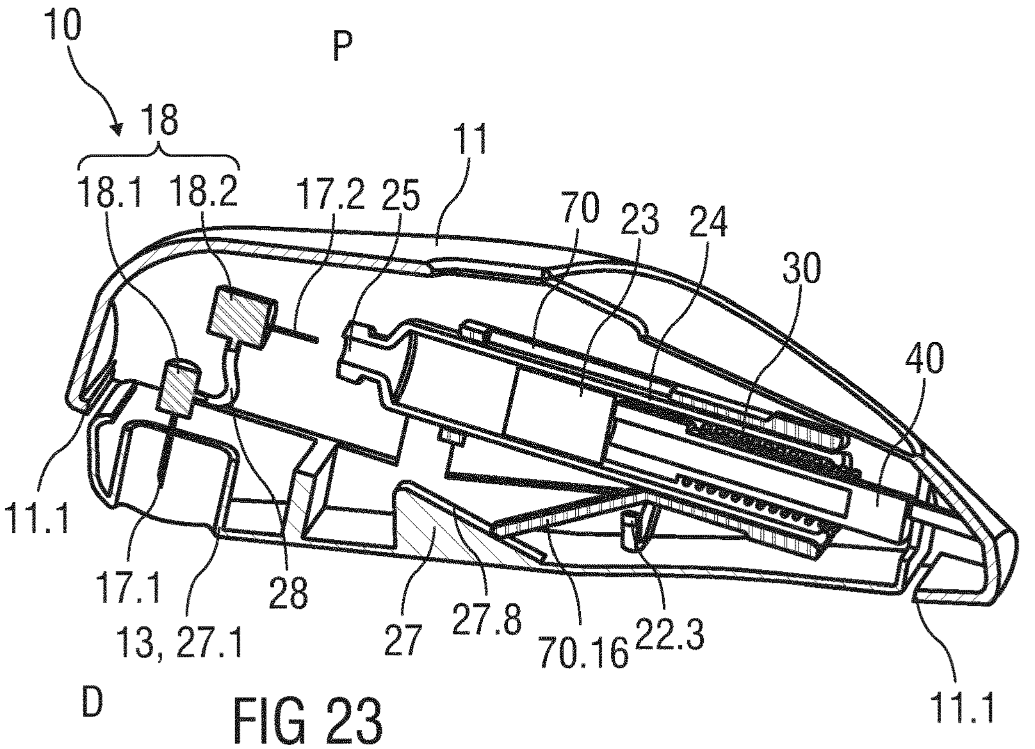
FIG. 23 is a schematic view of another exemplary embodiment of a drug delivery device prior to use.
Figure 24:
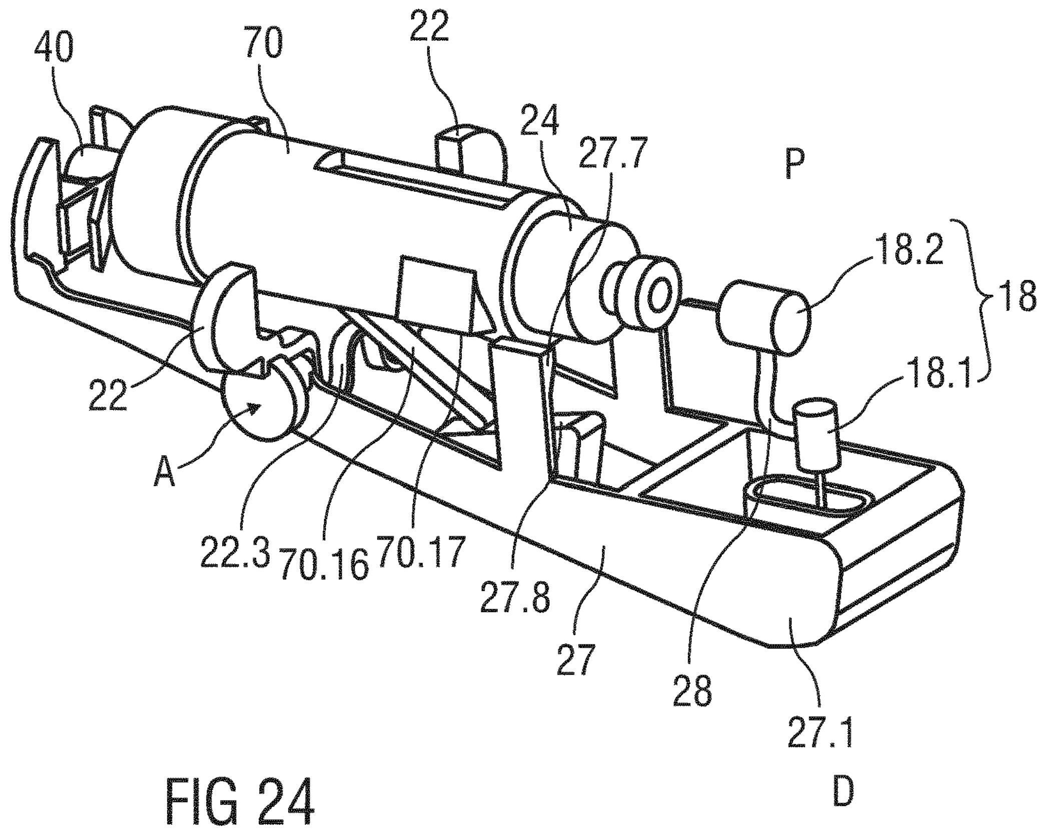
FIG. 24 is a schematic view of the drug delivery device.
Figure 25:
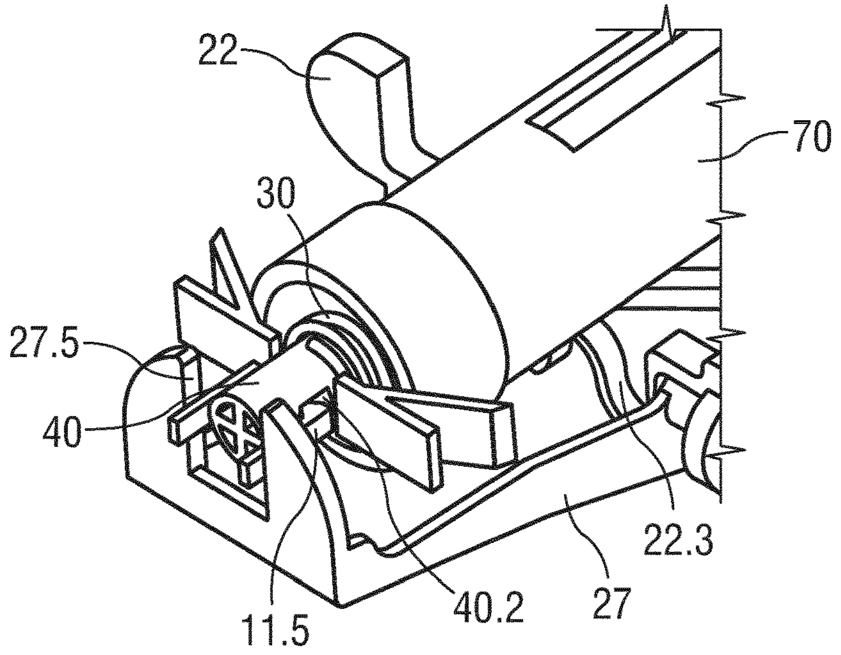
FIG. 25 is a schematic view of the drug delivery device.

FIGS. 23, 24 and 25 are schematic views of an exemplary embodiment of a drug delivery device 10 configured essentially like the one shown in FIG. 2.

The primary package 24 is slidable in the forward direction between a locking position and a release position. A body contact sensor 27 is pivoted about an axis A in the housing 11, e.g. a transversal axis, such that a contact part 27.1 of the body contact sensor 27 may extend from the distal surface 11.1 in an extended position and pivot about the axis A to be depressed toward or into the housing 11 in a retracted position. The body contact sensor 27 may be configured as a shroud 13 or comprise a shroud 13 for covering an extended needle 17, e.g. a first tip 17.1 thereof. A needle module 18 having a needle 17 with a first tip 17.1 and a second tip 17.2 is provided, the first tip 17.1 adapted to be extended from the distal surface 11.1 and the second tip adapted to point towards the primary package 24 to pierce a septum 25 thereof. The needle module 18 may be fixed in position within the housing 11 such that the first tip 17.1 protrudes from the distal surface 11.1. The needle module 18 may comprise a first sub-module 18.1 holding the first tip 17.1 and a second sub-module 18.2 holding the second tip 17.2. A fluid communication between the first tip 17.1 and the second tip 17.2 may be established by a flexible tube 28, e.g. a silicone tube. In an alternative embodiment, the needle 17 may comprise a single needle 17 bent at approximately 90 degrees. In another exemplary embodiment, the needle module 18 may comprise a solid block and the needle 17 may comprise two separate needle tips 17.1, 17.2 arranged at approximately 90 degrees to each other and connected within the solid block 19.

A drive spring 30 is arranged to bias the plunger 40 against the housing 11 to displace the piston 23 within the primary package 24 to deliver a dose.

A carrier 70 may be arranged within the housing 11 to contain the primary package 24 and to allow movement thereof essentially in parallel with the distal surface 11.1 towards the needle module 18.

The carrier 70 comprises a resilient carrier return beam 70.16 biased outwards from the carrier 70 and configured to engage the body contact sensor 27.

The plunger 40 comprises at least one aperture 40.2 adapted to be engaged by a respective resilient ramped locking pin 11.5 arranged on the housing 11 so as to lock the plunger 40 in a rearward position when the locking pin 11.5 is prevented from deflecting outwards by being outwardly supported by a support surface 27.5 on the body contact sensor 27 when the body contact part 27.1 extends from the housing 11 to cover the distal tip 17.1.

At least one button 22 may be arranged in the housing 11 and protrude through an aperture therein to prevent rotation of the body contact sensor 27 when the contact part 27.1 extends from the housing 11. The button 22 may extend in a lateral direction from the housing 11 and the button 22 and aperture in the housing 11 may have a non-circular shape preventing rotation of the button 22 within the aperture. A slot 27.6 may be arranged in the body contact sensor 27 near the axis A, wherein the button 22 is configured to engage in the slot 27.6 when not being depressed and when the contact part 27.1 extends from the housing 11 such that the body contact sensor 27 cannot rotate. Upon depression, the button 22 is configured to disengage the slot 27.6 releasing the body contact sensor 27 for rotation such that the contact part 27.1 can move towards the housing 11. In an exemplary embodiment, two buttons 22 are provided protruding in opposite lateral directions. The buttons 22 may be connected by a spring element 22.3 biasing the buttons 22 outwards. In an alternative embodiment, a different type of spring may be provided to bias the button 22 outwards.

The body contact sensor 27 may comprise at least one shroud lock beam 27.7 extending essentially in the proximal direction P and adapted to abut a respective locking surface 70.17 on the carrier 70 when the carrier 70 is in the forward position and when the contact part 27.1 extends from the housing 11. The shroud lock beam 27.7 may be resilient and the shroud lock beam 27.7 and/or the carrier 70 may be ramped to deflect the shroud lock beam 27.7 outwards over the locking surface 70.17 when the body contact sensor 27 is rotated into the extended position. Towards the end of this rotation the shroud lock beam 27.7 passes the locking surface 70.17 and relaxes inwards to abut the locking surface 70.17.

FIGS. 23, 24 and 25 show the drug delivery device 10 prior to use. The primary package 24 is in a rearward position. The buttons 22 are not depressed and thus engage in the slots 27.6 preventing the body contact sensor 27 from rotating into the retracted position. The first tip 17.1 is hidden within the sleeve 13 of the contact part 27.1. The carrier 70 is held in a rearward position by the carrier return beam 70.16 engaging a ramped surface 27.8 on the body contact sensor 27. The plunger 40 is held in a rearward position by the locking pins 11.5 engaging the apertures 40.2 and the support surface 27.5 outwardly supporting the locking pins 11.5.

Figure 26:
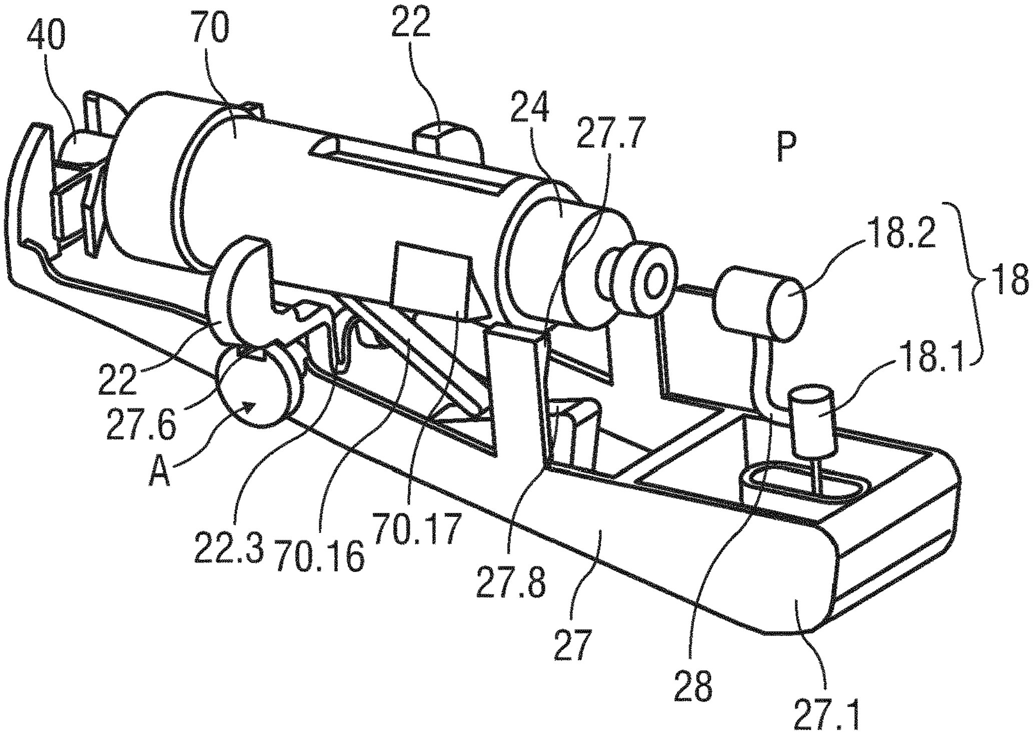
FIG. 26 is a schematic view of the drug delivery device during depression of buttons.

FIG. 26 is a schematic view of the drug delivery device 10 with the buttons 22 depressed. Upon depression, the buttons 22 disengage the slots 27.6 allowing rotation of the body contact sensor 27 about the axis A relative to the housing 11. However, the body contact sensor 27 is biased by the carrier return beam 70.16 such that the contact part 27.1 remains in the extended position.

Figure 27:
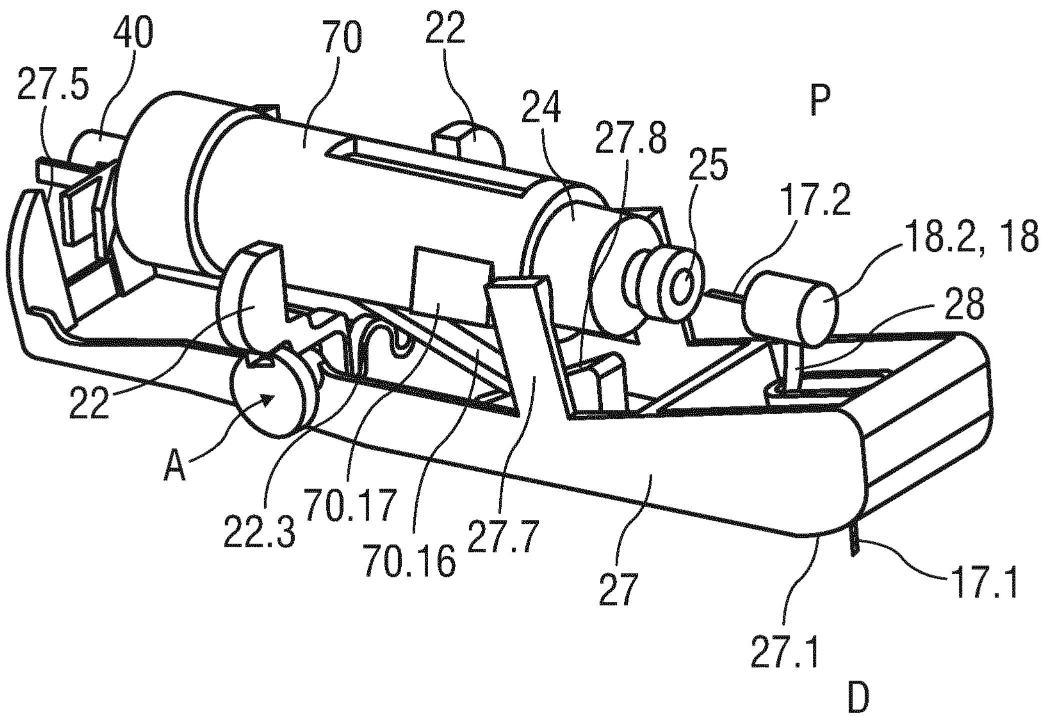
FIG. 27 is a schematic view of the drug delivery device with a body contact sensor in a retracted position.
Figure 28:
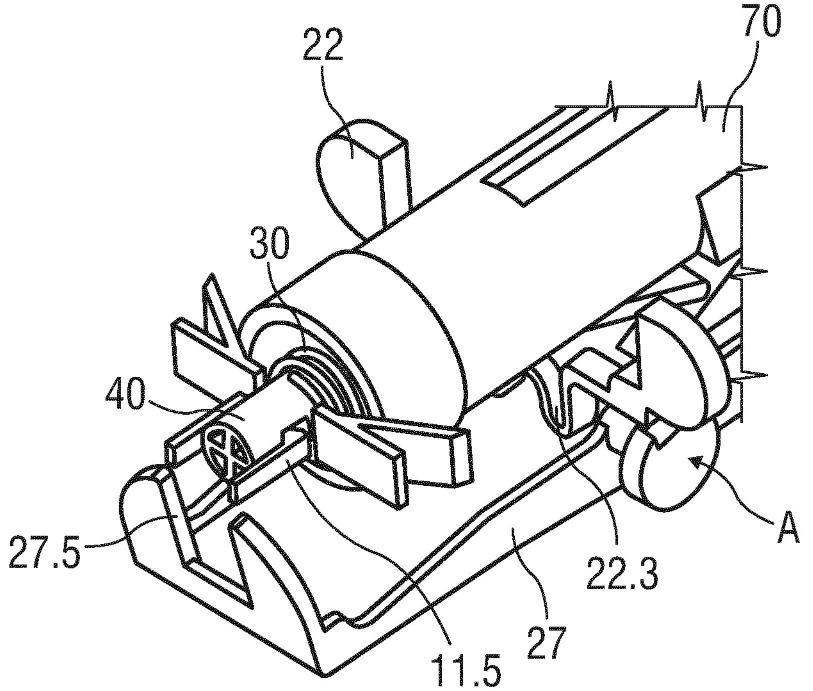
FIG. 28 is a schematic view of the drug delivery device with the body contact sensor in the retracted position.

FIGS. 27 and 28 are schematic views of the drug delivery device 10 placed with the body contact sensor 27 on an injection site. The housing 11 is tilted or rotated with respect to the body contact sensor 27 about the axis A such that the contact part 27.1 is moved into the retracted position thus exposing the distal tip 17.1 of the needle 17 and inserting it into an injection site. As the carrier 70 is still in the rearward position, the locking surface 70.17 does not interfere with the shroud lock beams 27.7 during this rotation. Due to the rotation the support surfaces 27.5 are removed from their position outwardly of the locking pins 11.5 allowing the locking pins 11.5 to deflect outwardly under the load of the drive spring 30 acting on the plunger 40 in the forward direction. Moreover, due to the rotation the carrier return beam 70.16 is deflected towards the carrier 70 and thus partly loaded.

Figure 29:
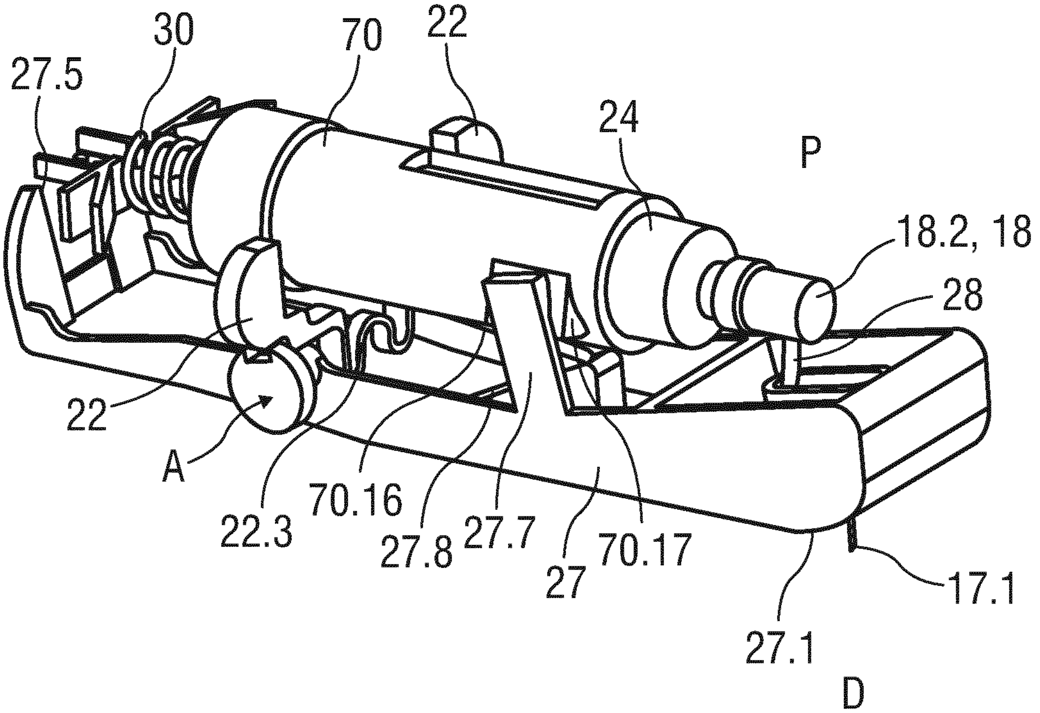
FIG. 29 is a schematic view of the drug delivery device with a plunger having been released.
Figure 30:
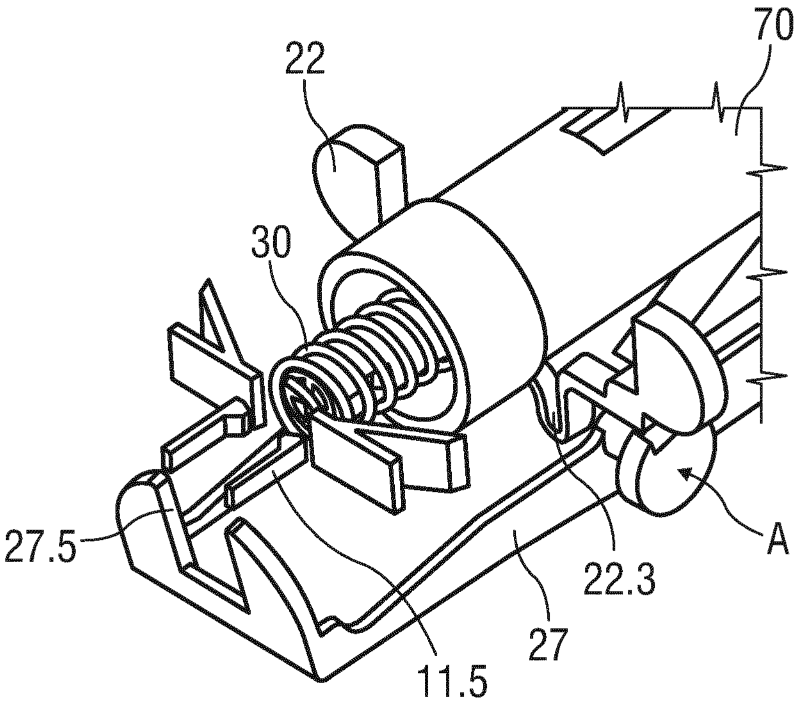
FIG. 30 is a schematic view of the drug delivery device with a plunger having been released.

FIGS. 29 and 30 are schematic view of the drug delivery device 10 with the plunger 40 having been released. As the support surfaces 27.5 have been removed from their position outwardly of the locking pins 11.5 the locking pins 11.5 are deflected outwardly under the load of the drive spring 30 acting on the plunger 40 in the forward direction. The plunger 40, piston 23, primary package 24 and carrier 70 are thus advanced forward such that the second tip 17.2 pierces the septum 25 and the shroud lock beam 27.2 becomes aligned with the locking surface 70.17 without engaging it. As soon as the septum 25 has been pierced by the second tip 17.2 the drive spring dispenses the dose by displacing the piston 23. Due to the forward movement of the carrier 70, the carrier return beam 70.16 travels up the ramped surface 27.8 and is thus further loaded.

Figure 31:
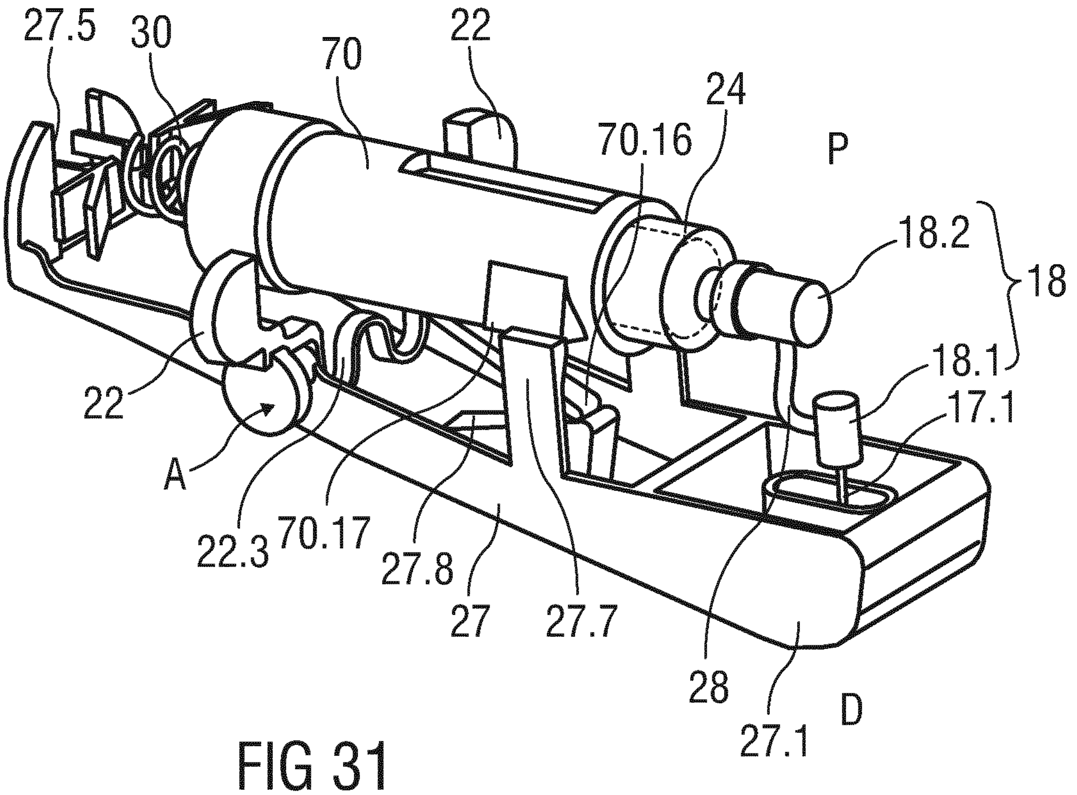
FIG. 31 is a schematic view of the drug delivery device after removal from an injection site.

FIG. 31 is a schematic view of the drug delivery device 10 having been removed from the injection site. As the contact part 27.1 is no longer being depressed, the loaded carrier return beam 70.16 relaxes and rotates the body contact sensor 27 such that the contact part 27.1 returns into the extended position again covering the first tip 17.1. During this rotation, the shroud lock beam 27.7 is ramped laterally outward by the carrier 70 and at the end of this rotation allowed to relax inward and to engage the locking surface 70.17 locking the body contact sensor 27 in the extended position.

Figure 32:
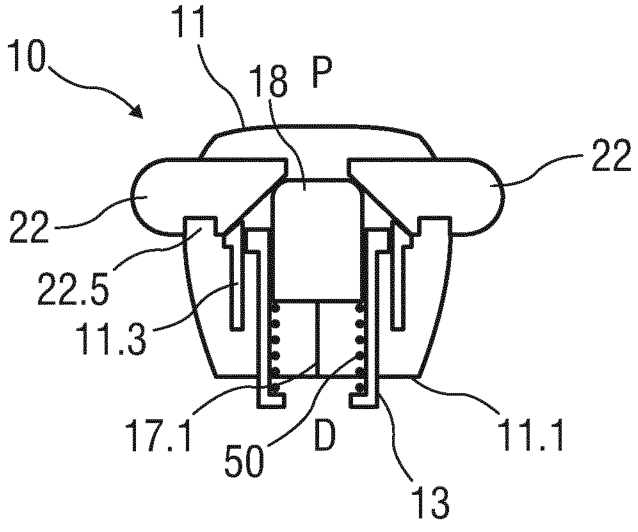
FIG. 32 is a schematic view of another exemplary embodiment of a drug delivery device prior to use.

FIG. 32 is a schematic view of an exemplary embodiment of a drug delivery device 10 configured essentially like the one shown in FIG. 2. A shroud 13 is slidable in the distal direction D and in the proximal direction P such that the shroud 13 may extend from the distal surface 11.1 in an extended position and may be depressed towards the housing 11 into a retracted position. A needle module 18 having a needle 17 with a first tip 17.1 and a second tip (not shown) is provided, the first tip 17.1 adapted to be extended from the distal surface 11.1 and the second tip adapted to point towards the primary package (not shown) to pierce a septum thereof. One or more laterally arranged trigger buttons 22 are arranged in the housing 11. The trigger buttons 22 comprise a respective cam surface 22.1 adapted to engage the needle module 18 to move it in the distal direction to make the first tip 17.1 protrude beyond the distal surface 11.1. The needle module 18 is biased in the proximal direction P against the shroud 13 by a shroud spring 50. One or more resilient clips 11.3 are arranged on the housing 11 configured to engage a respective one of the trigger buttons 22, e.g. the cam surface 22.1 thereof such that depression of the trigger button 22 deflects the resilient clip 11.3. The shroud 13 in its extended position is configured to inwardly support the resilient clips 11.3 preventing them from deflecting such that the trigger buttons 22 cannot be depressed. If the shroud 13 is in its retracted position, it ceases to inwardly support the resilient clips 11.3 allowing their inward deflection and hence depression of the trigger buttons 22. The trigger buttons 22 comprise a respective recess 22.5 adapted to receive the resilient clips 11.3 after the trigger buttons 22 have been depressed, deflected the resilient clips 11.3 and upon full depression of the trigger buttons 22 the resilient clips 11.3 have been allowed to relax into the recesses 22.5 to lock the trigger buttons 22 in their depressed position.

In FIG. 32, the shroud 13 is in its extended position blocking deflection of the resilient clips 11.3 and preventing depression of the trigger buttons 22. The needle module is in a retracted position with the first tip 17.1 hidden within the shroud 13 and within the housing 11 not protruding the distal surface 11.1.

Figure 33:
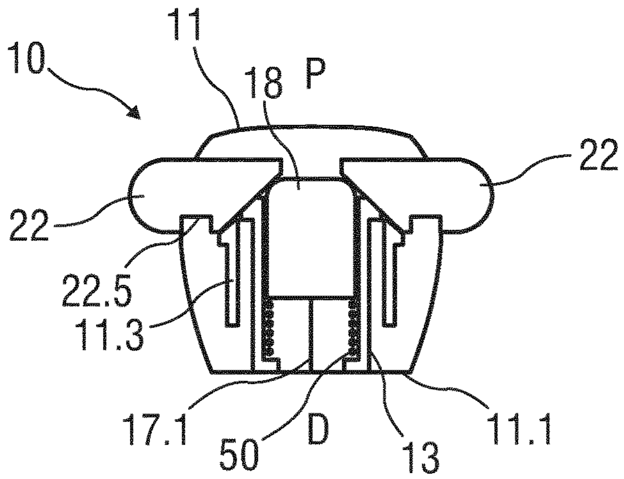
FIG. 33 is a schematic view of the drug delivery device with a shroud depressed towards a housing.

FIG. 33 is a schematic view of the drug delivery device 10 placed against an injection site with the shroud 13 ahead. The shroud 13 has hence been moved in the proximal direction into the retracted position thus ceasing to block deflection of the resilient clips 11.3 such that the trigger buttons 22 may be operated. If the user were to remove the drug delivery device 10 from the injection site at this point, the drug delivery device 10 would return to the state shown in FIG. 32.

Figure 34:
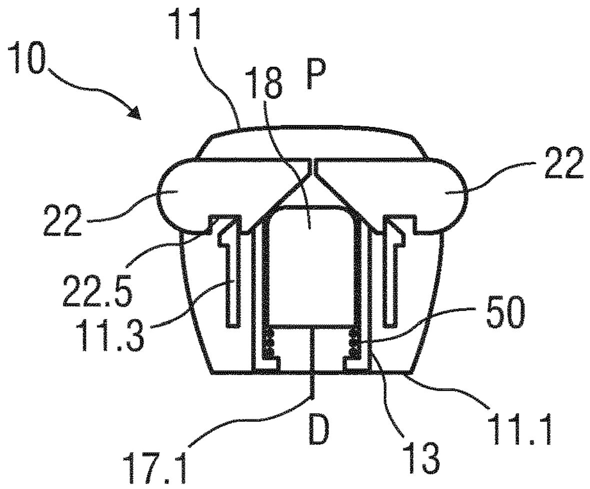
FIG. 34 is a schematic view of the drug delivery device during depression of buttons.

FIG. 34 is a schematic view of the drug delivery device 10 upon depression of the trigger buttons 22. The cam surface 22.1 engages the needle module 18 and moves it in the distal direction to make the first tip 17.1 protrude beyond the distal surface 11.1. Depression of the trigger button 22 furthermore deflects the resilient clip 11.3. Upon full depression of the trigger buttons 22 the resilient clips 11.3 have been allowed to relax into the recesses 22.5 to lock the trigger buttons 22 in their depressed position.

The primary package may now be pierced by the second tip of the needle and the drug may be suspended through the needle, e.g. by one of the mechanisms described above in the other embodiments or by any other suitable mechanism.

Figure 35:
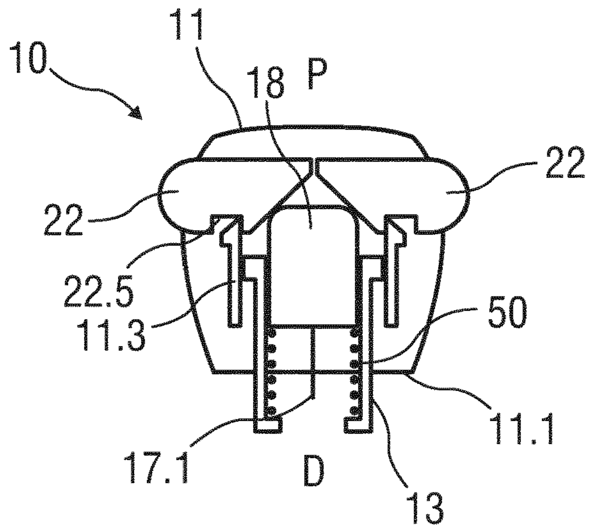
FIG. 35 is a schematic view of the drug delivery device after removal from an injection site.

FIG. 35 is a schematic view of the drug delivery device 10 having been removed from the injection site. The trigger buttons 22 remain in position after their depression as they are locked by the resilient clips 11.3 and thus, the needle module 18 also remains in its extended position with the first tip 17.1 protruding the distal surface 11.1. As depression of the shroud 13 and movement of the needle module 18 have compressed the shroud spring 50, the shroud spring 50 now advances the shroud 13 in the distal direction D into a second extended position in which the shroud 13 is moved farther in the distal direction D than in the extended position and therefore covers the distal tip 17.1. The shroud 13 may be locked in this position by a shroud lock mechanism as described above in the other embodiments or by any other suitable shroud lock mechanism.

Figure 36:
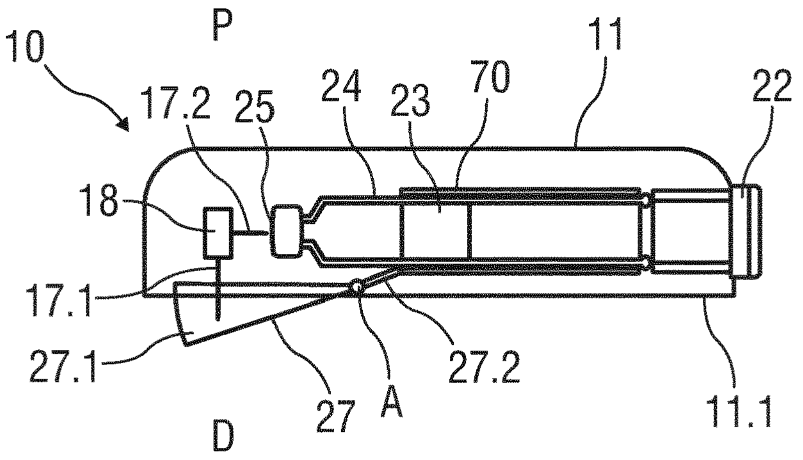
FIG. 36 is a schematic view of another exemplary embodiment of a drug delivery device prior to use.

FIG. 36 is a schematic view of an exemplary embodiment of a drug delivery device 10 configured essentially like the one shown in FIG. 2. A body contact sensor 27 comprising or configured as a shroud 13 is arranged rotatable about an axis A in the housing 11 such that a contact part 27.1 of the body contact sensor 27 may extend from the distal surface 11.1 in an extended position and may be depressed towards the housing 11 into a retracted position. A needle module 18 having a needle 17 with a first tip 17.1 and a second tip 17.2 is provided, the first tip 17.1 extending from the distal surface 11.1 and the second tip adapted to point towards the primary package 24 to pierce a septum 25 thereof. A carrier 70 may be arranged within the housing 11 to contain the primary package 24 and to allow movement thereof essentially in parallel with the distal surface 11.1 from a rearward position in which the septum 25 is spaced from the second tip 17.2 towards the needle module 18 into a forward position in which the second tip 17.2 pierces the septum 25. The body contact sensor 27 comprises an arm 27.2 adapted to engage the carrier 70 when the carrier 70 is in the rearward position and when the contact part 27.1 is in the extended position. The contact part 27.1 may be biased towards the extended position by a spring or a resilient component (not shown).

A trigger button 22 is arranged at a rearward end of the housing 11 adapted to engage or be coupled to the primary package 24 and/or the carrier 70 to move the carrier 70 and the primary package 24 forward from the rearward position upon depression of the trigger button 22. A drive spring (not shown) may be arranged to bias the piston 23 against the housing 11 or against the trigger button 22.

In FIG. 36, the contact part 27.1 is in its extended position such that the arm 27.2 engages the carrier 70 which is in the rearward position blocking forward movement of the carrier 70 and preventing depression of the trigger button 22.

Figure 37:
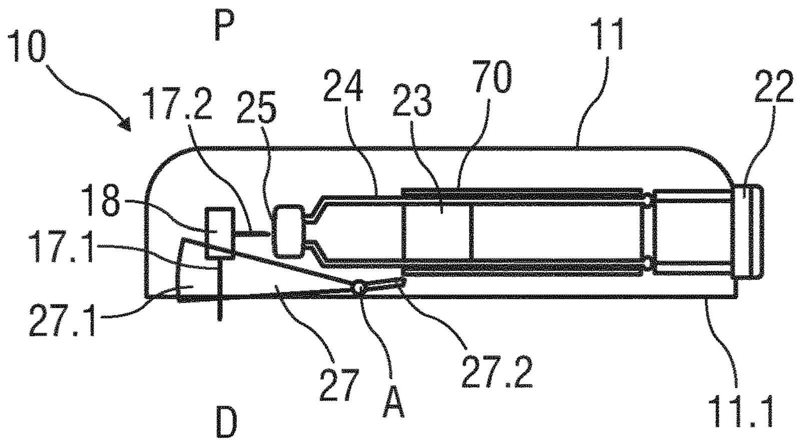
FIG. 37 is a schematic view of the drug delivery device with a body contact sensor in a retracted position.

FIG. 37 is a schematic view of the drug delivery device 10 placed against an injection site with the contact part 27.1 ahead. The contact part 27.1 has hence been moved in the proximal direction into the retracted position thereby also rotating the arm 27.2 which thus ceases to engage the carrier 70 such that the trigger button 22 may be operated. Due to depression of the contact part 27.1, the first tip 17.1 has been exposed and can pierce the injection site. If the user were to remove the drug delivery device 10 from the injection site at this point, the drug delivery device 10 would return to the state shown in FIG. 36 due to the bias of the contact part 27.1 towards the extended position.

Figure 38:
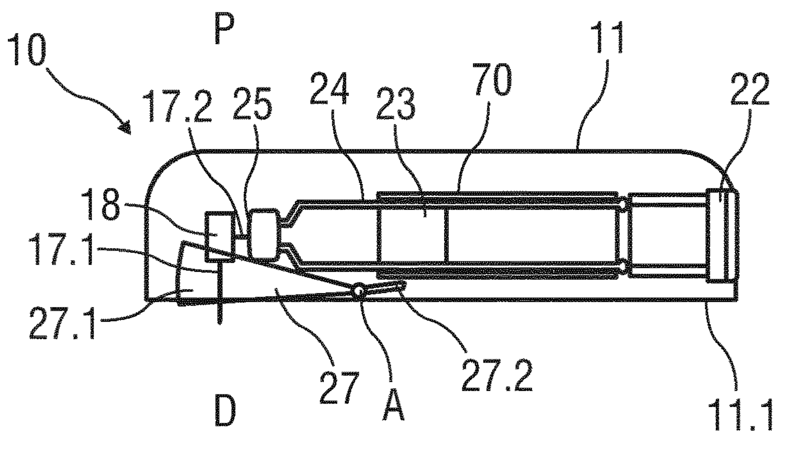
FIG. 38 is a schematic view of the drug delivery device during depression of a button.

FIG. 38 is a schematic view of the drug delivery device 10 upon depression of the trigger button 22. Depression of the trigger button 22 moves the carrier 70 and primary package 24 forward such that the septum 25 of the primary package is pierced by the second tip 17.2 of the needle 17 and the drug may be suspended through the needle, e.g. by the drive spring (not shown).

If the drug delivery device 10 is removed from the injection site, the contact part 27.1 may be moved into the extended position again due to being biased. The contact part 27.1 may be locked in this position by a shroud lock mechanism as described above in the other embodiments or by any other suitable shroud lock mechanism.

Figure 39:
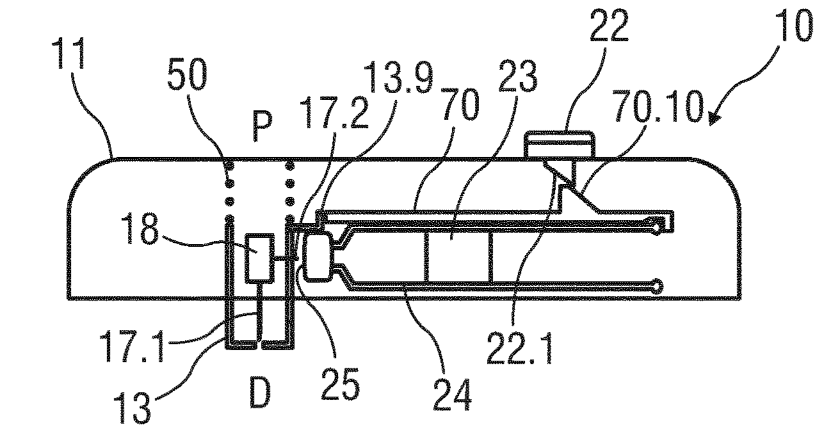
FIG. 39 is a schematic view of another exemplary embodiment of a drug delivery device prior to use.

FIG. 39 is a schematic view of an exemplary embodiment of a drug delivery device 10 configured essentially like the one shown in FIG. 2. A shroud 13 is arranged slidable in the housing 11 between an extended position and a retracted position. A needle module 18 having a needle 17 with a first tip 17.1 and a second tip 17.2 is provided, the first tip 17.1 extending from the distal surface 11.1 and the second tip 17.2 adapted to point towards the primary package 24 to pierce a septum 25 thereof. A carrier 70 may be arranged within the housing 11 to contain the primary package 24 and to allow movement thereof essentially in parallel with the distal surface 11.1 from a rearward position in which the septum 25 is spaced from the second tip 17.2 towards the needle module 18 into a forward position in which the second tip 17.2 pierces the septum 25. The shroud 13 is biased towards the extended position by a shroud spring 50. The shroud 13 comprises a stop 13.9 adapted to engage the carrier 70 when the carrier 70 is in the rearward position and when the shroud 13 is in the extended position such that the carrier 70 cannot advance.

A trigger button 22 is arranged in the housing 11, e.g. on a proximal side thereof adapted to engage the carrier 70 to move the carrier 70 and the primary package 24 forward from the rearward position upon depression of the trigger button 22. The trigger button 22 may comprise a ramp 22.1 and/or the carrier 70 may comprise a ramp 70.10 for this purpose.

A drive spring (not shown) may be arranged to bias the piston 23 against the housing 11.

In FIG. 39, the shroud 13 is in its extended position such that the stop 13.9 engages the carrier 70 which is in the rearward position blocking forward movement of the carrier 70 and preventing depression of the trigger button 22.

Figure 40:
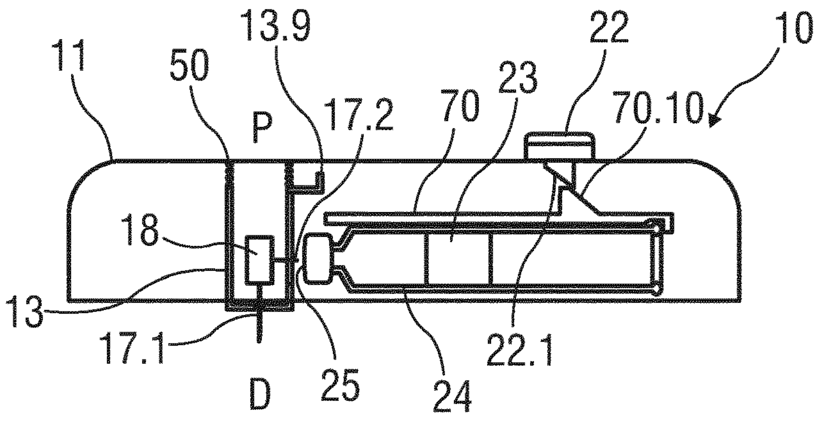
FIG. 40 is a schematic view of the drug delivery device with a shroud depressed towards a housing.

FIG. 40 is a schematic view of the drug delivery device 10 placed against an injection site with the shroud 13 ahead. The shroud 13 has hence been moved in the proximal direction P into the retracted position thereby removing the stop 13.9 from his abutment with the carrier 70 such that the trigger button 22 may be operated. Due to depression of the shroud 13, the first tip 17.1 has been exposed and can pierce the injection site. If the user were to remove the drug delivery device 10 from the injection site at this point, the drug delivery device 10 would return to the state shown in FIG. 39 due to the bias of the shroud 13 towards the extended position.

Figure 41:
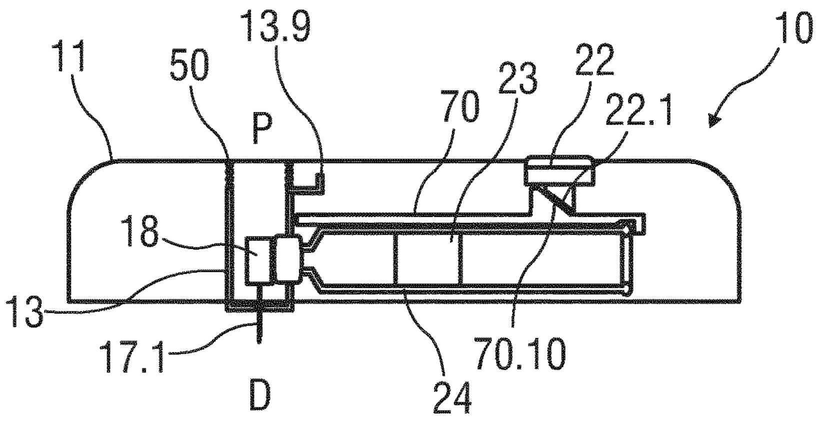
FIG. 41 is a schematic view of the drug delivery device during depression of a button.

FIG. 41 is a schematic view of the drug delivery device 10 upon depression of the trigger button 22. Depression of the trigger button 22 ramps the carrier 70 and primary package 24 forward such that the septum 25 of the primary package is pierced by the second tip 17.2 of the needle 17 and the drug may be suspended through the needle, e.g. by the drive spring (not shown).

If the drug delivery device 10 is removed from the injection site, the shroud 13 may be moved into the extended position again due to being biased. The shroud 13 may be locked in this position by a shroud lock mechanism as described above in the other embodiments or by any other suitable shroud lock mechanism.

Figure 42:
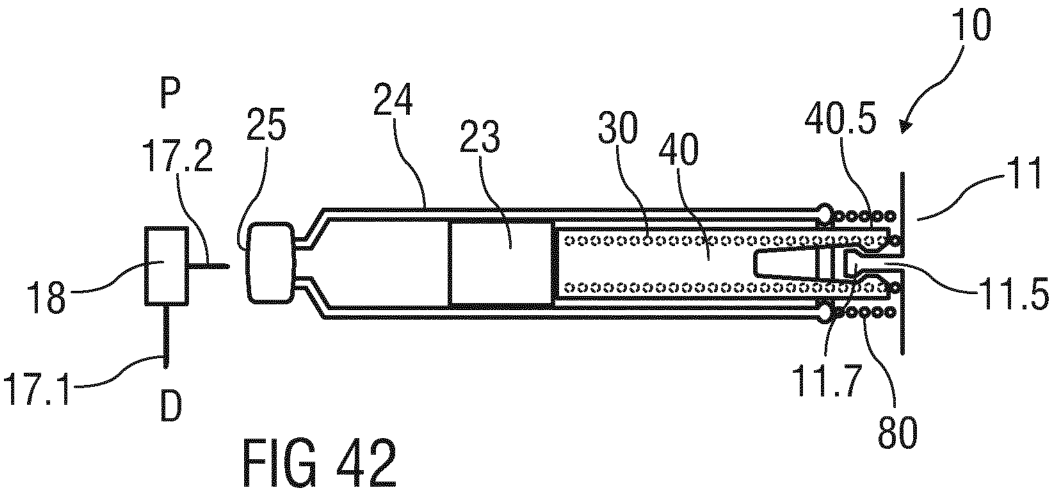
FIG. 42 is a schematic detail view of another exemplary embodiment of a drug delivery device prior to use.

FIG. 42 is a schematic detail view of an exemplary embodiment of a drug delivery device 10 which may be combined with any one of the above described embodiments, in particular the embodiment of FIGS. 13 to 22.

A needle module 18 having a needle 17 with a first tip 17.1 and a second tip 17.2 is provided, the first tip 17.1 extending from the distal surface and the second tip 17.2 adapted to point towards the primary package 24 to pierce a septum 25 thereof. A carrier (not shown) may be arranged within the housing 11 to contain the primary package 24 and to allow movement thereof essentially in parallel with the distal surface from a rearward position in which the septum 25 is spaced from the second tip 17.2 towards the needle module 18 into a forward position in which the second tip 17.2 pierces the septum 25.

A drive spring 30 may be arranged to bias a plunger 40 configured to displace the piston 23 forwards against the housing 11. The plunger 40 comprises one or more rearwardly extending prongs 40.5 configured to engage a locking pin 11.5 on the housing 11, the locking pin 11.5 having a slub 11.7. The slub 11.7 and/or the prongs 40.5 are ramped so as to deflect the prongs 40.5 outwards to disengage them from the locking pin 11.5 under the force from the drive spring 30. When the primary package 24 is in the rearward position, the prongs 40.5 are at least partly received within the primary package 24 such that they are prevented from outwardly deflecting and can thus not disengage the locking pin 11.5. A further spring 80, e.g. a carrier spring 80, may be arranged to bias the carrier of primary package 24 against the housing 11 in the forward direction.

In FIG. 42, the primary package 24 is in the rearward position such that the septum 25 is spaced from the second tip 17.2. The prongs 40.5 are engaged to the locking pin 11.5 and cannot deflect to disengage it. The primary package 24 may be held in the rearward position by any one of the respective mechanisms shown in the embodiments above or by another suitable mechanism.

Figure 43:
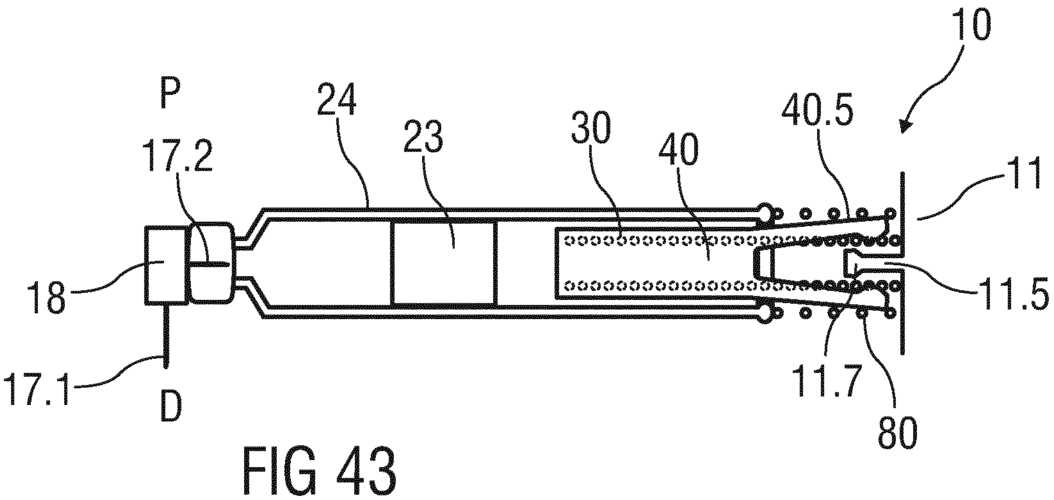
FIG. 43 is a schematic detail view of the drug delivery device after release of a primary package to be moved forward.

FIG. 43 is a schematic detail view of the drug delivery device 10 after release of the primary package 24 to be moved forward. Due to the release, the primary package 24 can advance forward, driven by the spring 80, and the second tip 17.2 pierces the septum 25.

Due to the movement of the primary package 24 and the plunger 40 remaining in position, the prongs 40.5 are no longer positioned within the primary package 24 so that they can deflect outward to disengage them from the locking pin 11.5 under the force from the drive spring 30 thus releasing the plunger 40 to be moved forward.

Figure 44:
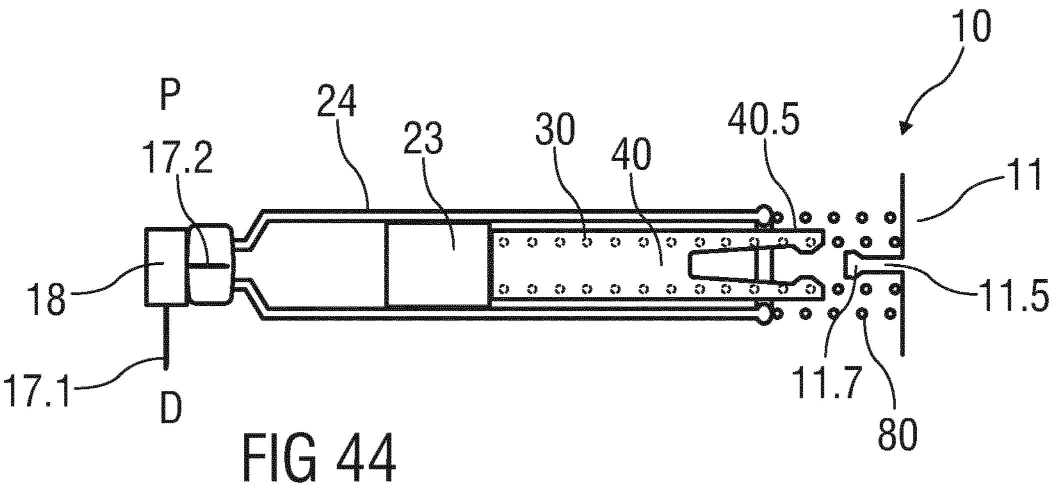
FIG. 44 is a schematic detail view of the drug delivery device after release of a plunger.

FIG. 44 is a schematic detail view of the drug delivery device 10 after release of the plunger 40. The plunger 40 has been moved forward by the drive spring 30 and abutted the piston 23 to subsequently dispense the dose by displacing the piston 23.

In an exemplary embodiment, the second tip 17.2 may have a higher inner diameter than the first tip 17.1.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and $F(ab')_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

Further embodiments are described in the following:

Embodiment 1. A drug delivery device (10), comprising a housing (11) adapted to receive a primary package (24), the housing (11) comprising a distal surface (11.1) adapted to be placed against an injection site and a proximal surface (11.2) opposite the distal surface (11.1), the proximal surface (11.2) adapted to be held in the palm of a user's hand during drug delivery, the housing (11) having a flat form-factor in such a manner that a first extension of the housing (11) between the distal surface (11.1) and the proximal surface (11.2) is less than at least one extension at right angles to the first extension.

Embodiment 2. The drug delivery device (10) of embodiment 1, comprising an injection needle (17) configured to be connected or connectable to a primary package (24) received within the housing (11), wherein the needle (17) comprises a first tip (17.1) which is:

- either configured to be extended beyond the distal surface (11.1) by a manual operation, or
- to extend beyond the distal surface (11.1) and to be covered by a shroud (13) configured to be retracted to expose the first tip (17.1) by a manual operation.

Embodiment 3. The drug delivery device (10) of embodiment 1 or 2, wherein a mounting axis of the primary package (24) is essentially at right angles with respect to the first extension.

Embodiment 4. The drug delivery device (10) according to any one of embodiments 1 to 3, wherein the distal surface (11.1) is non-adhesive.

Embodiment 5. The drug delivery device (10) according to any one of the preceding embodiments, wherein the distal surface (11.1) is rigid.

Embodiment 6. The drug delivery device (10) according to any one of the preceding embodiments, wherein the housing (11) comprises at least one window (11*a*) through which the primary package (24) can be monitored.

Embodiment 7. The drug delivery device (10) of embodiment 6, wherein the window (11*a*) is arranged in the proximal surface (11.2) and/or in a lateral surface of the housing (11).

Embodiment 8. The drug delivery device (10) according to any one embodiments 2 to 7, wherein the needle (17) is part of a needle module (18) and comprises a second tip (17.2) adapted to pierce a septum (25) on a primary package (24) received within the housing (11).

Embodiment 9. The drug delivery device (10) of embodiment 8, wherein the needle (17) is a single needle bent at approximately 90 degrees or wherein the first tip (17.1) and the second tip (17.2) are separate from each other and arranged at approximately 90 degrees to each other and connected within a solid block (19) or via a flexible tube (28).

Embodiment 10. The drug delivery device (10) of embodiment 2 to 9, wherein the needle (17) is movable between a retracted position with the needle (17) hidden within the housing (11) and an extended position with the needle (17) extending through the distal surface (11.1).

Embodiment 11. The drug delivery device (10) according to embodiment 10, comprising a trigger adapted to move the needle (17) from the retracted position to the extended position upon manual operation of the trigger.

Embodiment 12. The drug delivery device (10) according to embodiment 11, wherein the trigger comprises at least one of a shroud (13), at least one button (22) and a body contact sensor (27).

Embodiment 13. The drug delivery device (10) according to embodiment 12, wherein the at least one button (22) is disposed at the proximal surface (11.2) or at at least one lateral surface or at a rear surface of the housing (11).

Embodiment 14. The drug delivery device (10) according to embodiment 12 or 13, wherein the body contact sensor (27) or the shroud (13) is disposed at the distal surface (11.1), wherein the shroud (13) is adapted to cover the needle (17) when the needle (17) is in the extended position.

Embodiment 15. The drug delivery device (10) according to any one of the embodiments 10 to 14, wherein the needle (17) is adapted to be retracted from the extended position into the retracted position upon removal of the distal surface (11.1) from an injection site or upon release of the trigger.

Embodiment 16. The drug delivery device (10) according to any one of embodiments 9 to 15, comprising a carrier (70) adapted to mount a primary package (24) and movable substantially in parallel with the distal surface (11.1) between a rearward position, in which the second tip (17.2) is spaced from the septum (25) and a forward position, in which the second tip (17.2) pierces the septum (25).

Embodiment 17. The drug delivery device (10) according to embodiment 16, wherein the trigger is configured to initiate movement of the carrier (70) from the rearward position to the forward position.

Embodiment 18. The drug delivery device (10) according to any one of embodiments 12 to 17, wherein the button (22) is adapted to be locked prior to operation of the shroud (13) or body contact sensor (27) preventing operation of the button (22), wherein the button (22) is adapted to be unlocked upon operation of the shroud (13) or body contact sensor (27) allowing operation of the button (22).

Embodiment 19. The drug delivery device (10) according to any one of the preceding embodiments, comprising a drive spring (30) adapted to apply a force in a forward direction to a piston (23) of the primary package (24).

Embodiment 20. The drug delivery device (10) of embodiment 19, comprising a plunger (40) adapted to propagate the force from the drive spring (30) to the piston (23).

Embodiment 21. The drug delivery device (10) according to any one of the preceding embodiments, comprising a primary package (24) containing a medicament.

Embodiment 22. The drug delivery device (10) according to any one of the preceding embodiments, wherein a latch chassis (26) is arranged to receive a forward end of the primary package (24).

Embodiment 23. The drug delivery device (10) according to any one of embodiments 8 to 22, wherein the needle module (18) is coupled with or integrated in a button (22) such that depression of the button (22) in the distal direction (D) moves the needle module (18) in the distal direction (D).

Embodiment 24. The drug delivery device (10) according to embodiment 23, wherein the button (22) comprises a rearwardly directed sleeve (22.4) and the second tip (17.2) is essentially centered within this sleeve (22.4).

Embodiment 25. The drug delivery device (10) according to embodiment 24, wherein the button (22) has a proximal position when not being depressed in which the sleeve (22.4) is not coaxial with the primary package (24) such that the primary package (24) abuts an edge of the sleeve (22.4) and cannot advance forward, wherein the button (22) has a distal position when being depressed in which the sleeve (22.4) is coaxial with the primary package (24) such that the primary package (24) can advance forward into the sleeve (22.4) and the second tip (17.2) pierces the septum (25).

Embodiment 26. The drug delivery device (10) according to any one of the preceding embodiments, wherein a shroud spring (50) is arranged to bias the shroud (13) in the distal direction (D) against the housing (11) or against the needle module (18) or against the button (22).

Embodiment 27. The drug delivery device (10) according to any one of embodiments 12 to 26, wherein at least one resilient button locking beam (20.6) is arranged on the housing (11), the button locking beam (20.6) having a ramped inward protrusion (20.7) adapted to engage in a respective recess (22.5) within the button (22) through a slot (13.1) in the shroud (13).

Embodiment 28. The drug delivery device (10) according to embodiment 27, wherein the shroud (13) comprises a support section (13.14) outwardly from the button locking beam (20.6) which, when the shroud (13) is in a first extended position protruding the distal surface (11.1) and/or in a second extended position protruding the distal surface (11.1) further than in the first extended position, outwardly supports the button locking beam (20.6) preventing it from deflecting outwards.

Embodiment 29. The drug delivery device (10) according to any one of embodiments 12 to 28, wherein at least one shroud locking beam (20.8) is arranged on the housing (11), the shroud locking beam (20.8) having a ramped inward protrusion (20.9) adapted to engage a surface on the shroud (13) and a surface on the button (22) through a window (13.15) in the shroud (13).

Embodiment 30. The drug delivery device (10) according to any one of the preceding embodiments, wherein at least one shroud rib (13.16) is arranged on the shroud (13) and configured to abut the housing (11) to prevent the shroud (13) from moving distally beyond a second extended position.

Embodiment 31. The drug delivery device (10) according to any one of embodiments 23 to 30, wherein the button (22) has a proximal position when not being depressed in which the second tip (17.2) is not coaxial with the primary package (24), wherein the button (22) has a distal position when being depressed in which the second tip (17.2) is coaxial with the primary package (24) such that the second tip (17.2) can pierce the septum (25).

Embodiment 32. The drug delivery device (10) according to any one of embodiments 16 to 31, wherein the carrier (70) comprises at least one resilient forward arm (70.1) having a front surface (70.11) configured to abut on a stop (20.5) on the housing (11) thus maintaining the carrier (70) and the primary package (24) in a rearward position.

Embodiment 33. The drug delivery device (10) according to embodiment 32, wherein the shroud (13) comprises at least one resilient arm (13.17) having an outward protrusion (13.18) configured to be in the vicinity of one respective forward arm (70.1) when the shroud (13) is in the retracted position such that outward deflection of the resilient arm (13.17) causes outward deflection of the forward arm (70.1) so that the front surface (70.11) disengages the stop (20.5) allowing the carrier (70) to move forward.

Embodiment 34. The drug delivery device (10) according to embodiment 33, wherein the button (22) comprises at least one ramped protrusion (22.6) configured to engage the resilient arm (13.17) upon depression of the button (22) into the distal position when the shroud (13) is in the retracted position such that the resilient arm (13.17) is outwardly deflected and disengages the forward arm (70.1) from the stop (20.5).

Embodiment 35. The drug delivery device (10) according to any one of embodiments 32 to 34, wherein the forward arms (70.1) comprises at least one snap feature adapted to engage at least one corresponding feature on the shroud (13) when the carrier (70) is in the forward position and when the shroud (13) is advanced into the extended position.

Embodiment 36. The drug delivery device (10) according to any one of embodiments 12 to 35, wherein the body contact sensor (27) is pivoted about an axis (A) in the housing (11) such that a contact part (27.1) of the body contact sensor (27) extends from the distal surface (11.1) in an extended position and pivot about the axis (A) to be depressed toward or into the housing (11) in a retracted position.

Embodiment 37. The drug delivery device (10) according to any one of embodiments 12 to 36, wherein the the body contact sensor (27) is configured as a shroud (13) or comprises a shroud (13) for covering the first tip (17.1).

Embodiment 38. The drug delivery device (10) according to any one of embodiments 8 to 37, wherein the needle module (18) is fixed in position within the housing (11) such that the first tip (17.1) protrudes from the distal surface (11.1).

Embodiment 39. The drug delivery device (10) according to any one of embodiments 8 to 38, wherein the needle module (18) comprises a first sub-module (18.1) holding the first tip (17.1) and a second sub-module (18.2) holding the second tip (17.2).

Embodiment 40. The drug delivery device (10) according to any one of embodiments 16 to 39, wherein the carrier (70) comprises a resilient carrier return beam (70.16) biased outwards from the carrier (70) and configured to engage the body contact sensor (27).

Embodiment 41. The drug delivery device (10) according to any one of embodiments 20 to 40, the plunger (40) comprises at least one aperture (40.2) adapted to be engaged by a respective resilient ramped locking pin (11.5) arranged on the housing (11) so as to lock the plunger (40) in a rearward position when the locking pin (11.5) is prevented from deflecting outwards by being outwardly supported by a support surface (27.5) on the body contact sensor (27) when the body contact sensor (27) is in an extended position.

Embodiment 42. The drug delivery device (10) according to any one of embodiments 12 to 41, wherein the at least one button (22) protrudes through an aperture in the housing (11) to prevent rotation of the body contact sensor (27) when the body contact sensor (27) is in an extended position.

Embodiment 43. The drug delivery device (10) according to embodiment 42, wherein the at least one button (22) extends in a lateral direction from the housing (11) and the button (22) and aperture in the housing (11) have a non-circular shape preventing rotation of the button (22) within the aperture.

Embodiment 44. The drug delivery device (10) according to embodiment 42 or 43, wherein a slot (27.6) is arranged in the body contact sensor (27) near the axis (A), wherein the button (22) is configured to engage in the slot (27.6) when not being depressed and when the body contact sensor (27) is in the extended position such that the body contact sensor (27) cannot rotate, wherein, upon depression, the button (22) is configured to disengage the slot (27.6) releasing the body contact sensor (27) for rotation.

Embodiment 45. The drug delivery device (10) according to any one of embodiments 12 to 44, wherein a spring element (22.3) is provided to bias the button (22) to extend from the housing (11).

Embodiment 46. The drug delivery device (10) according to any one of embodiments 12 to 45, wherein the body contact sensor (27) comprises at least one shroud lock beam (27.7) extending essentially in the proximal direction (P) and adapted to abut a respective locking surface (70.17) on the carrier (70) when the carrier (70) is in the forward position and when the body contact sensor (27) is in the extended position.

Embodiment 47. The drug delivery device (10) according to embodiment 46, wherein the shroud lock beam (27.7) is resilient and the shroud lock beam (27.7) and/or the carrier (70) are/is ramped to deflect the shroud lock beam (27.7) outwards over the locking surface (70.17) when the body contact sensor (27) is rotated into the extended position.

Embodiment 48. The drug delivery device (10) according to any one of the embodiments 12 to 47, wherein one or more laterally arranged trigger buttons (22) are arranged in the housing (11), wherein the trigger buttons (22) comprise a respective cam surface (22.1) adapted to engage the needle module (18) to move it in the distal direction to make the first tip (17.1) protrude beyond the distal surface (11.1).

Embodiment 49. The drug delivery device (10) according to any one of embodiments 12 to 48, wherein one or more resilient clips (11.3) are arranged on the housing (11) configured to engage a respective one of the trigger buttons (22) such that depression of the trigger button (22) deflects the resilient clip (11.3).

Embodiment 50. The drug delivery device (10) according to embodiment 49, wherein the shroud (13) in its extended position is configured to inwardly support the resilient clips (11.3) preventing them from deflecting such that the at least one trigger button (22) cannot be depressed, wherein the shroud (13) in its retracted position ceases to inwardly support the resilient clips (11.3) allowing their inward deflection and hence depression of the trigger buttons (22).

Embodiment 51. The drug delivery device (10) according to any one of embodiments 49 or 50, wherein the trigger buttons (22) comprise a respective recess (22.5) adapted to receive the resilient clips (11.3) after the trigger buttons (22) have been depressed, deflected the resilient clips (11.3) and, upon full depression of the trigger buttons (22), the resilient clips (11.3) have been allowed to relax into the recesses (22.5) to lock the trigger buttons (22) in their depressed position.

Embodiment 52. The drug delivery device (10) according to any one of embodiments 16 to 51, wherein the body contact sensor (27) comprises an arm (27.2) adapted to engage the carrier (70) when the carrier (70) is in the rearward position and when the contact part (27.1) is in the extended position.

Embodiment 53. The drug delivery device (10) according to any one of embodiments 12 to 52, wherein the body contact sensor (27) is biased towards the extended position by a spring or a resilient component.

Embodiment 54. The drug delivery device (10) according to any one of embodiments 12 to 53, wherein the trigger button (22) is arranged at a rearward end of the housing (11) adapted to engage or be coupled to the primary package (24) and/or the carrier (70) to move the carrier (70) and/or the primary package (24) forward from the rearward position upon depression of the trigger button (22).

Embodiment 55. The drug delivery device (10) according to any one of embodiments 16 to 54, wherein the shroud (13) comprises a stop (13.9) adapted to engage the carrier (70) when the carrier (70) is in the rearward position and when the shroud (13) is in the extended position such that the carrier (70) cannot advance forward.

Embodiment 56. The drug delivery device (10) according to any one of embodiments 16 to 55, wherein the trigger button (22) is adapted to engage the carrier (70) or the primary package (24) to move the carrier (70) and/or the primary package (24) forward from the rearward position upon depression of the trigger button (22).

Embodiment 57. The drug delivery device (10) according to embodiment 56, wherein the trigger button (22) comprises a ramp (22.1) and/or the carrier (70) may comprise a ramp (70.10) for mutually engaging the trigger button (22) and the carrier (70).

Embodiment 58. The drug delivery device (10) according to any one of embodiments 20 to 57, wherein the plunger (40) comprises one or more rearwardly extending prongs (40.5) configured to engage a slub (11.7) on a locking pin (11.5) on the housing (11).

Embodiment 59. The drug delivery device (10) according to embodiment 58, wherein the slub (11.7) and/or the prongs (40.5) are ramped so as to deflect the prongs (40.5) outwards to disengage them from the locking pin (11.5) under the force from the drive spring (30).

Embodiment 60. The drug delivery device (10) according to embodiment 58 or 59, wherein, when the primary package (24) is in the rearward position, the prongs (40.5) are at least partly received within the primary package (24) such that they are prevented from outwardly deflecting and can thus not disengage the locking pin (11.5).

Embodiment 61. The drug delivery device (10) according to any one of embodiments 16 to 47, wherein a carrier spring (80) is arranged to bias the carrier (70) towards the needle module (18).

Embodiment 62. The drug delivery device (10) according to any one of embodiments 20 to 61, wherein the drive spring (30) is arranged within the plunger (40) or about the plunger (40).

Embodiment 63. The drug delivery device (10) according to any one of the preceding embodiments, wherein a noise component (90) is arranged to provide an audible feedback when the drug has been at least nearly fully expelled from the primary package (24).

Embodiment 64. The drug delivery device (10) according to any one of embodiments 2 to 63, wherein one or more clips are provided on the housing (11) and/or on the shroud (13) to engage the shroud (13) to the housing (11) when the shroud (13) is extended to cover the needle (17).

Embodiment 65. The drug delivery device (10) according to any one of embodiments 61 to 63, wherein the carrier spring (80) is arranged laterally from the carrier (70) or about the carrier (70).

LIST OF REFERENCES

10 drug delivery device
11 housing
11.1 distal surface
11.2 proximal surface
11.3 resilient clip
11.5 locking pin
11.7 slub
11*a* window
12 cap assembly
13 shroud
13.1 slot
13.9 stop
13.14 support section
13.15 window
13.16 shroud rib
13.17 resilient arm
13.18 outward protrusion
13.19 latch window
17 needle
17.1 first tip
17.2 second tip
18 needle module
18.1 first sub-module
18.2 second sub-module
19 solid block
20 distal region
20.5 stop
20.6 button locking beam
20.7 inward protrusion
20.8 shroud locking beam
20.9 inward protrusion
21 proximal region
22 button
22.1 ramp/cam surface
22.3 spring element
22.4 sleeve
22.5 recess
22.6 protrusion
23 piston
24 primary package
24.1 forward end
25 septum
26 latch chassis
26.1 latch boss
27 body contact sensor
27.1 contact part
27.2 arm
27.5 support surface
27.6 slot
27.7 shroud lock beam
27.8 ramped surface
28 flexible tube
30 drive spring
40 plunger
40.2 aperture
40.5 prong
50 shroud spring
70 carrier
70.1 forward arm
70.10 ramp
70.11 front surface
70.16 carrier return beam
70.17 locking surface
80 carrier spring
A axis
D distal direction
P proximal direction
X longitudinal axis

The invention claimed is:

1. A drug delivery device comprising:

a housing adapted to receive a primary package, wherein the housing comprises a distal surface adapted to be placed against an injection site and a proximal surface opposite the distal surface, wherein the proximal surface is adapted to be held in a palm of a hand of a user during drug delivery, and wherein the housing has a flat form-factor in such a manner that a first extension of the housing between the distal surface and the proximal surface is less than a second extension at right angles to the first extension;

an injection needle comprising a first tip and a second tip, wherein the injection needle is configured to be connected to the primary package received within the housing;

a carrier adapted to mount the primary package such that the primary package does not move relative to the carrier when mounted;

a shroud adapted to be movable between an extended position and a retracted position relative to the housing; and a trigger button wherein the second tip is adapted to pierce a septum on the primary package, wherein the carrier is movable relative to the housing between:

a rearward position in which the second tip is spaced from the septum, and a forward position in which the second tip pierces the septum;

wherein the shroud is configured to limit a movement of the carrier to the forward position when the shroud is in the extended position, wherein the shroud comprises a stop adapted to engage the carrier for limiting the movement of the carrier to the forward position, when the shroud is in the extended position, and wherein the stop is adapted to prevent operation of the trigger button when the shroud is in the extended position, and wherein the stop is adapted to allow operation of the trigger button when the shroud is in the retracted position.

2. The drug delivery device of claim 1, wherein the shroud is slidable between an extended position and a retracted position, wherein the shroud extends beyond the distal surface of the housing prior to use of the drug delivery device, and wherein the shroud covers the first tip after removal of the drug delivery device from an injection site.

3. The drug delivery device of claim 1, wherein a mounting axis of the primary package is essentially at right angles with respect to the first extension.

4. The drug delivery device of claim 1, wherein the distal surface is non-adhesive.

5. The drug delivery device of claim 1, wherein the distal surface is rigid.

6. The drug delivery device of claim 1, wherein the injection needle is a single needle bent at approximately 90 degrees, or wherein the first tip and the second tip are separate from each other and arranged at approximately 90 degrees with respect to each other and connected within a solid block or via a flexible tube.

7. The drug delivery device of claim 1, wherein the trigger button is disposed at the proximal surface of the housing, at a lateral surface of the housing, or at a rear surface of the housing.

8. The drug delivery device of claim 1, wherein the trigger button is adapted to be unlocked upon operation of the shroud to allow operation of the trigger button.

9. The drug delivery device of claim 1, further comprising a drive spring adapted to apply a force in a forward direction to a piston of the primary package.

10. The drug delivery device of claim 1, further comprising the primary package.

11. The drug delivery device of claim 10, wherein the primary package contains a medicament.

12. The drug delivery device of claim 1, wherein a needle module is coupled with or integrated in the trigger button.

13. The drug delivery device of claim 12, wherein depression of the trigger button in the distal direction moves the needle module in the distal direction.

14. The drug delivery device of claim 13, wherein a shroud spring is arranged to bias the shroud in the distal direction against the housing, against the needle module, or against the trigger button.

15. The drug delivery device of claim 1, wherein the first tip is configured either to: be extended beyond the distal surface by a manual operation, or extend beyond the distal surface and be covered by the shroud, wherein the shroud is configured to be retracted to expose the first tip by the manual operation.

16. The drug delivery device of claim 1, comprising an energy source configured to provide a force for delivering drug from the primary package.

* * * * *